(12) United States Patent
Fukuyama et al.

(10) Patent No.: US 7,417,145 B2
(45) Date of Patent: Aug. 26, 2008

(54) PROCESS FOR TOTAL SYNTHESIS OF ECTEINASCIDINS AND INTERMEDIATES THEREFOR

(75) Inventors: Tohru Fukuyama, Tokyo (JP); Toshiyuki Kan, Tokyo (JP)

(73) Assignee: Japan Science and Technology Agency, Saitama-ken (JP)

( * ) Notice: Subject to any disclaimer, the term of this patent is extended or adjusted under 35 U.S.C. 154(b) by 443 days.

(21) Appl. No.: 10/498,367

(22) PCT Filed: Sep. 20, 2002

(86) PCT No.: PCT/JP02/09690

§ 371 (c)(1), (2), (4) Date: Jun. 10, 2004

(87) PCT Pub. No.: WO03/064432

PCT Pub. Date: Aug. 7, 2003

(65) Prior Publication Data

US 2005/0043308 A1 Feb. 24, 2005

(30) Foreign Application Priority Data

Jan. 29, 2002 (JP) ............................... 2002-019360

(51) Int. Cl.
- *C07D 241/36* (2006.01)
- *C07D 405/06* (2006.01)
- *C07D 317/50* (2006.01)
- *C07D 413/04* (2006.01)

(52) U.S. Cl. .................. 544/338; 544/342; 544/153; 544/343; 544/344; 544/377

(58) Field of Classification Search ............... 544/340, 544/338, 342
See application file for complete search history.

(56) References Cited

OTHER PUBLICATIONS

Endo et. al. (J. Am. Chem. Soc., 2002, 124, 6552-6554).*
Endo, "Total Synthesis of Ecteinascidin 743", J. Am. Chem. Soc. 2002, vol. 124, 6552-6554.
Corey, "Enantioselective Total Synthesis of Ecteinascidin 743", J. Am. Chem. Soc. 1996, vol. 118, 9202-9203.
Tohma, "Synthesis of Optically Active alpha-Arylglycines: Stereoselective Mannich-Type Reaction with a New Chiral Template", Synlett 2001, No. 7, 1179-1181.
Endo, "Synthetic Study on Ecteinascidin 743 Starting From D-Glucose", Synlett 1999, No. 7, 1103-1105.
Hinterding, "Synthesis and In Vitro Evaluation of the Ras Farnesyltransferase Inhibitor Pepticinnamin E", Angew. Chem. Int. Ed. 1998, 37, No. 9 1236-1239.
Cuevas C, et al., "Synthesis of Ecteinascidin ET-743 and Phthalascidin PT-650 . . . ", Organic Letters, ACS, Washington, DC, US, vol. 2, No. 16, 2000, pp. 2545-2548.
Zhou, et al., "Studies Directed to the Total Synthesis of ET 743 . . . ", Organic Letters, ACS, Washington, DC, US, vol. 4, No. 1, 2002, pp. 43-46.

* cited by examiner

*Primary Examiner*—James O. Wilson
*Assistant Examiner*—Susanna Moore
(74) *Attorney, Agent, or Firm*—Hahn & Voight; Roger C. Hahn

(57) ABSTRACT

An intermediate compound for total synthesis of ecteinascidins comprising, a compound represented by general formula 2 having thioether group at C4 site, and the substituent $R_2$ of $N_{12}$ site is trichloroethoxicarbonyl (Troc) to which various substituents can be introduced by mild condition, further having a 10-membered ring structure which can be converted to a ring of other numbered members.

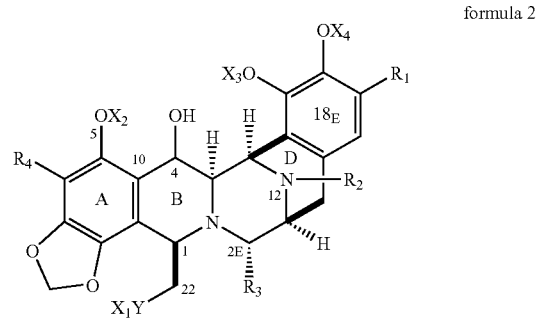

formula 2

4 Claims, No Drawings

PROCESS FOR TOTAL SYNTHESIS OF ECTEINASCIDINS AND INTERMEDIATES THEREFOR

FIELD OF THE INVENTION

The present invention relates to an intermediate compounds useful for the total synthesis of ecteinascidin 743 (hereinafter shortened to Et 743) having high antineoplastic activity, the analogous structural compounds to Et 743 and the method for synthesis of Et 743.

BACKGROUND OF THE INVENTION

Ecteinascidins is a group of marine alkaloid having antineoplasticity which is isolated from the extracted products from marine tunicate habitat of Caribbean sea by very small amount. Among the ecteinascidins, since Et 743 has a very strong antineoplastic activity, the investigation to put it into practical use as a carcinostatic agent is limited, and the phase II clinical tests are now carried out in ten several countries in Europe and America. It is known that Et 743 has an effect to depress the proliferation of cancer cells by 10 to 100 times more potent than(IC50=0.1–1 nM) Toxol, Camptotesin, Adriamycin or Mitomycin which are currently used carcinostatic agent.

From the back ground mentioned above, various investigations for synthesis were carried out, however, the complete synthesis was only reported by Prof. E. J. Corey of Harvard University in U.S.A. (J. Am. Chem. Soc. 1996, 118, 9202-9203, reference document A).

In the process of synthesis of the total synthesis disclosed in Document A (refer to page 9202), the feature of the process is existing in the point that Et 743 is synthesized from the analogous compound to the compound represented by general formula 1 of the present invention via intermediates 4 and 8. That is, according to said process, $C_4$ site of ring B (regarding indication of ring, and the sites of atoms composing 6-members ring, refer to general formula 1) which composes 6-members ring is formed from the intermediate 4 at the first step. And, since to the atom $C_4$ composing B ring of 6-membered ring H which lacks reactivity is bonded, it becomes necessary to have an oxidation reaction to $C_4$ site on B ring. This oxidation reaction is not effective and is carried out by harsh condition, therefore, the production by industrial scale is difficult and also the yield is not good. Further, since atom $N_{12}$ site of the synthesized intermediate is substituted by alkyl group which lacks reactivity, in this case substituted by methyl group, it is not suited to the synthesis for various compounds. Although the total synthesis was reported, the supplying source of Et 743 is still depending on the natural sample whose supplying amount is very scarce, therefore, the establishment of the method for a large scale production of Et 743 is desired by accomplishing an effective synthesizing process.

Since, Et 743 is known as a medicine having high antineoplasticity, and phthalascidin induced from the intermediate product at the synthesis of Et 743 displays same activity to Et 743, the establishment of the effective and mild method for synthesis of Et 743 and analogous compound thereof is strongly desired.

Therefore, the subject of the present invention is basically to accomplish the effective method for total synthesis of Et 743, further, to provide not only Et 743 but also analogous compounds.

To dissolve the subject, the present invention tried the retrosynthetic analysis, which promises easy synthesis. And it will be possible to form B ring by ring forming reaction at ortho position of phenol which composes A ring to inner molecular aldehyde in a generated compound by 4-8 reaction. Further, the inventors of the present invention considered that the generated compound by 4-8 reaction will be possible to synthesize based on the polycondensation reaction of general formula 4, and general formula 5 via a compound of general formula 3, the total synthesis of Et 743, which is the aimed compound, by way of the compounds represented by general formulae 5, 4, 3, 2 and 1 and the specific structure of general formulae 1 and 2. And confirmation of the synthetic route enabled providing the analogous compound of Et 743.

DISCLOSURE OF THE INVENTION

The first one of the present invention is an intermediate compound for total synthesis of ecteinascidins comprising, a compound represented by general formula 1 having thioether group at $C_4$ site, and the substituent $R_2$ of $N_{12}$ site is trichloroethoxicarbonyl to which various substituents can be introduced by mild condition, further having 10 members ring structure which can be converted to a ring of other numbered members,

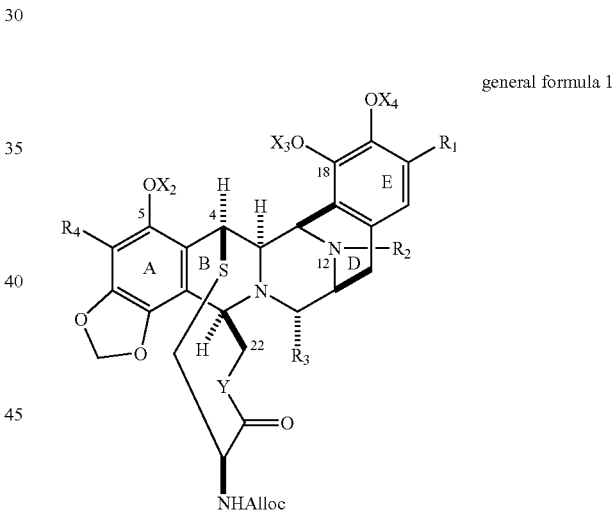

general formula 1 wherein, Y is O or NH, $X_2$, $X_3$ and $X_4$ are independently selected from the group consisting of H or alkyl group of carbon number 4 or less, alkoxyalkyl group, allyl group, or alkyl or arylsulfonyl group, $R_1$ and $R_4$ is H or alkyl group of carbon number 4 or less, $R_2$ is alkoxycarbonyl group which can be substituted by halogen, lower alkyl sulfonyl or aryl sulfonyl group and $R_3$ is nitrile or OH.

The second one of the present invention is a method for synthesis of the compound of general formula 1 having the processes displayed by the reaction 5-1 which is transforming reaction of $C_{18}$ hydroxyl group to allyl ether and $C_{22}$ acetyl group to hydroxyl group, the reaction 5-2 which is introducing reaction of cysteine derivatives into $C_{22}$ acetyl group and the reaction 5-3 which is $C_4$ thioetherification reaction and transforming reaction of $C_5$ hydroxyl group to acetyl group, wherein Y is O, $X_2$ is Ac, $X_3$ is H, $R_1$ is Me, $R_2$ is Troc, $R_3$ is CN, and $X_4$ and $R_4$ are same as to general formula 1.

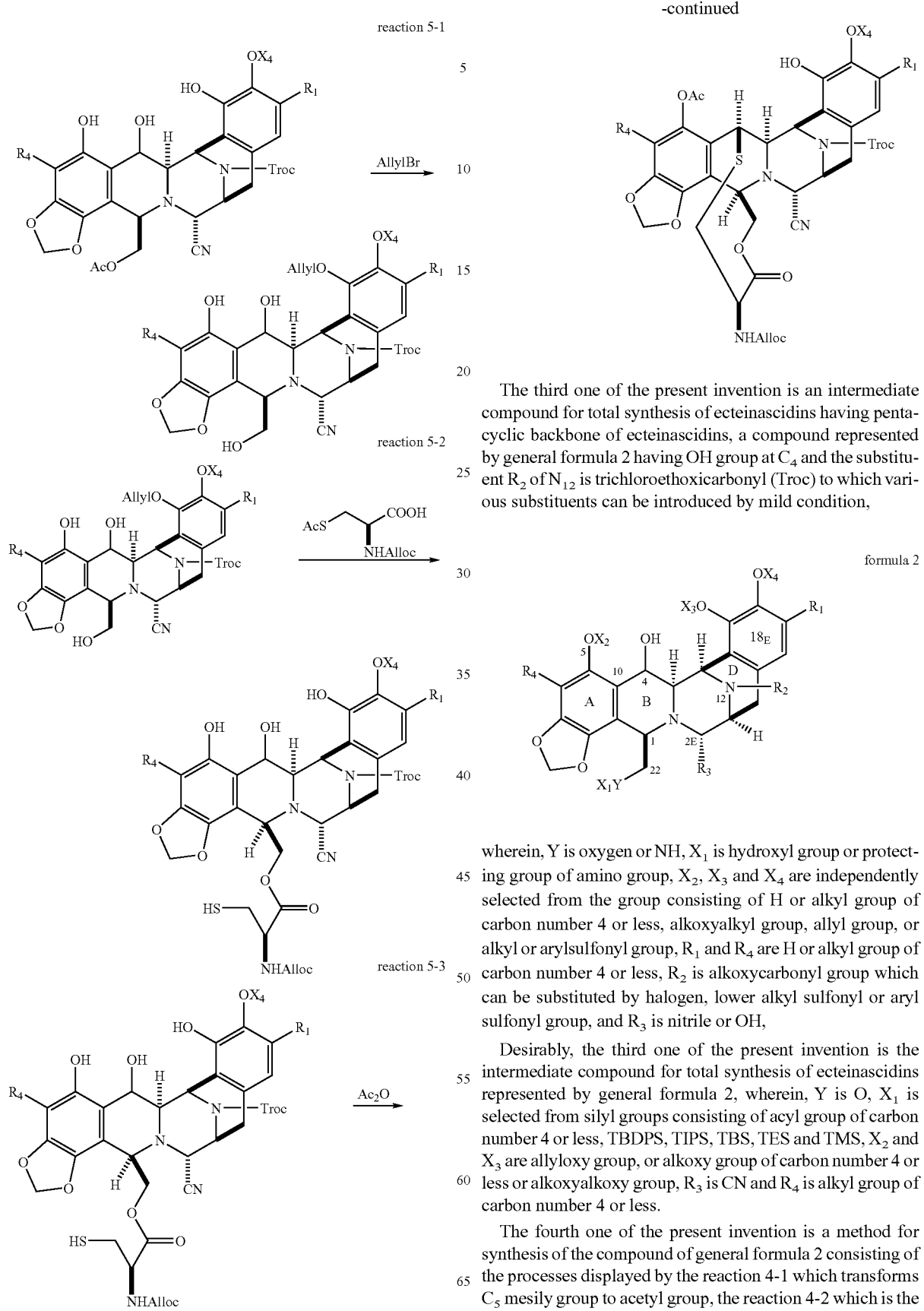

The third one of the present invention is an intermediate compound for total synthesis of ecteinascidins having pentacyclic backbone of ecteinascidins, a compound represented by general formula 2 having OH group at $C_4$ and the substituent $R_2$ of $N_{12}$ is trichloroethoxicarbonyl (Troc) to which various substituents can be introduced by mild condition, wherein, Y is oxygen or NH, $X_1$ is hydroxyl group or protecting group of amino group, $X_2$, $X_3$ and $X_4$ are independently selected from the group consisting of H or alkyl group of carbon number 4 or less, alkoxyalkyl group, allyl group, or alkyl or arylsulfonyl group, $R_1$ and $R_4$ are H or alkyl group of carbon number 4 or less, $R_2$ is alkoxycarbonyl group which can be substituted by halogen, lower alkyl sulfonyl or aryl sulfonyl group, and $R_3$ is nitrile or OH, Desirably, the third one of the present invention is the intermediate compound for total synthesis of ecteinascidins represented by general formula 2, wherein, Y is O, $X_1$ is selected from silyl groups consisting of acyl group of carbon number 4 or less, TBDPS, TIPS, TBS, TES and TMS, $X_2$ and $X_3$ are allyloxy group, or alkoxy group of carbon number 4 or less or alkoxyalkoxy group, $R_3$ is CN and $R_4$ is alkyl group of carbon number 4 or less.

The fourth one of the present invention is a method for synthesis of the compound of general formula 2 consisting of the processes displayed by the reaction 4-1 which transforms $C_5$ mesily group to acetyl group, the reaction 4-2 which is the transforming reaction of $N_{12}$ t-butoxycarbonyl group to trichloroethyl group, the reaction of 4-3 which is hydration reaction of $C_{3-4}$ double bond, the reaction 4-4 which is the transforming reaction of $C_4$ hydroxyl group to TBS group and transforming reaction of $C_{22}$ and $C_5$ acetyl group to hydroxyl group, the reaction 4-5 which is transforming reaction of $C_5$ hydroxyl group to benzyl group, reaction 4-6 which is reduction reaction of $C_{21}$ amide and ring closing reaction of oxazolidine, the reaction 4-7 which is ring opening reaction of oxazolidine and transforming reaction of $C_{22}$ hydroxyl group to acetyl group, the reaction 4-8 which is oxidation reaction of $C_2$ hydroxyl group to aldehyde and the reaction 4-9 which is transforming reaction of $C_5$, $C_{18}$ benzyloxy groups to hydroxyl group and ring forming reaction of B ring, wherein Y is O, $X_2$ is H, $X_3$ is H, $R_3$ is CN, $X_1$ is Ac, $X_4$, $R_1$ and $R_4$ are same to the general formula 2.

-continued

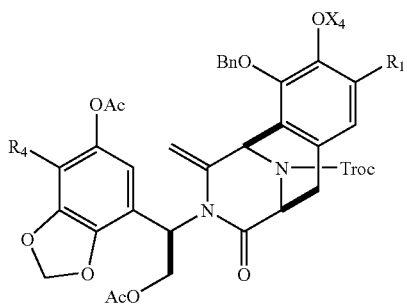

reaction 4-1

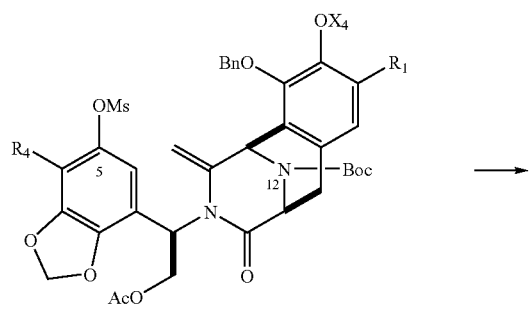

reaction 4-3

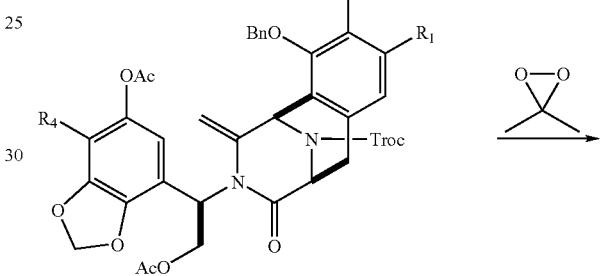

reaction 4-2

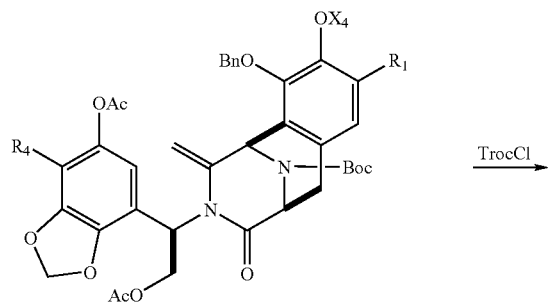

reaction 4-4

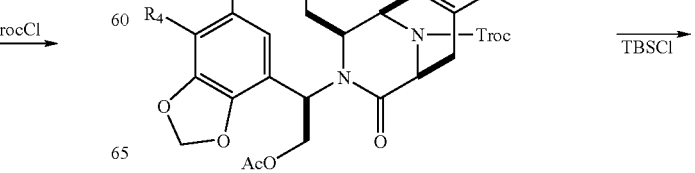

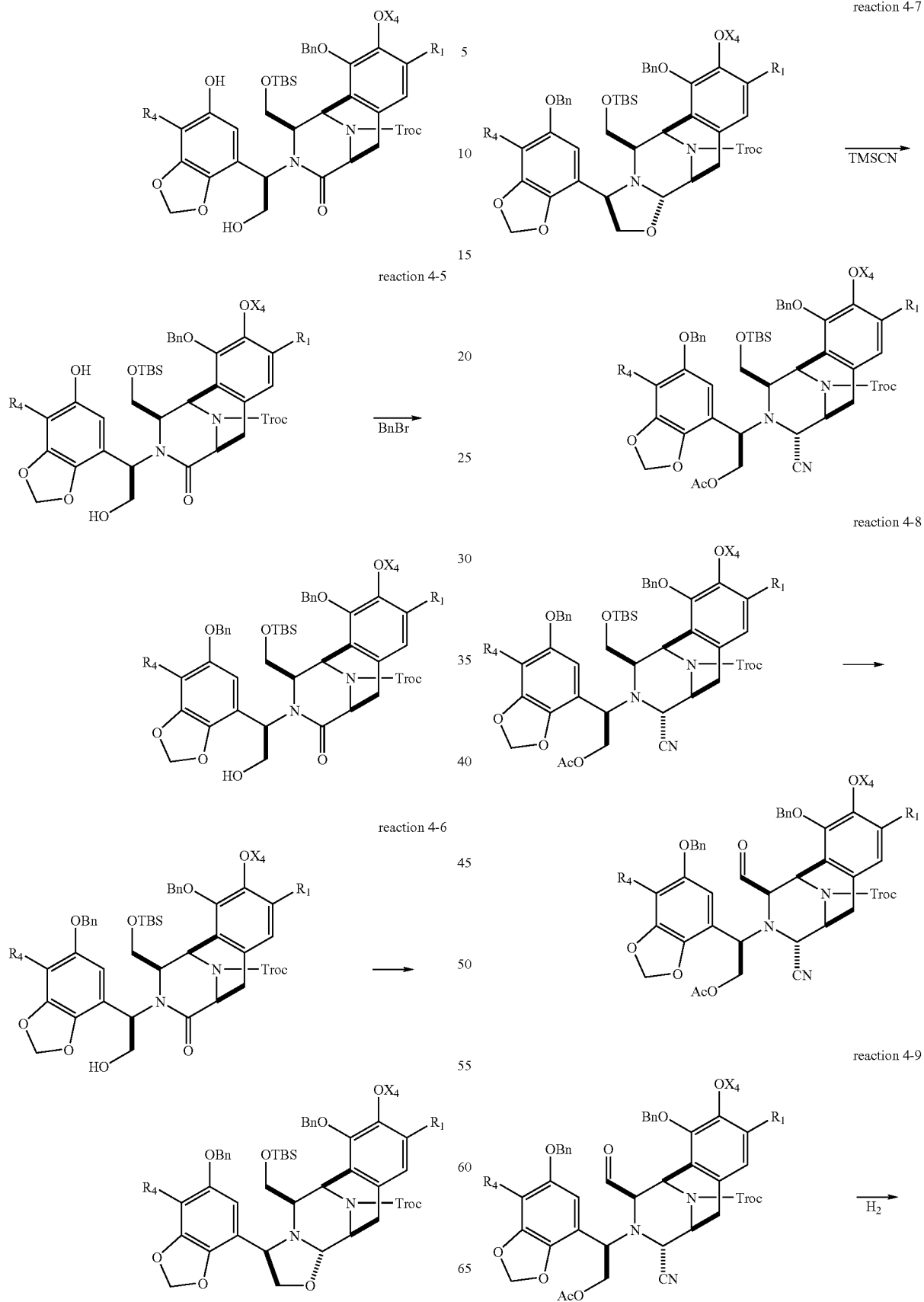

-continued

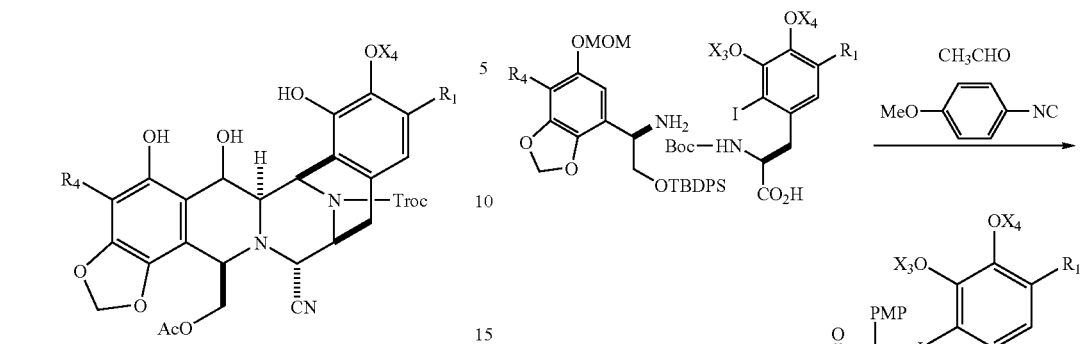

The fifth one of the present invention is an intermediate compound for the compound of general formula 2 represented by general formula 3 comprising the carbon locating at $C_{10}$ site at pentacyclic backbone of ecteinascidins of general formula 2 is bonded with H.

general formula 3

In general formula 3, $R_1$, $R_2$ and $R_4$, $X_1$-$X_4$ are same as to these of general formula 2.

Desirably, the fifth one of the present invention is the intermediate compound for the compound represented by general formula 3, wherein Y is O, $X_1$ is selected from silyl groups consisting of acyl group of carbon number 4 or less, TBDPS, TIPS, TBS, TES and TMS, $X_2$ and $X_3$ are allyloxy group, or alkoxy group of carbon number 4 or less or alkoxy-alkoxy group, $R_3$ is CN and $R_4$ is alkyl group of carbon number 4 or less.

The sixth one of the present invention is the method for synthesis of the compound of general formula 3 consisting of the processes displayed by the reaction 3-1 which is the Ugi's 4 components condensation reaction, the reaction 3-2 which is the transforming reaction of $C_{22}$ TBTPS group to acetyl group, the reaction 3-3 which is C ring forming reaction, the reaction 3-4 which is transforming reaction of $C_5$ hydroxyl group to mesyl group, the reaction 3-5 which is reduction of $C_{11}$ amide and dehydration reaction of $C_{3-4}$ double bond and reaction 3-6 which is the construction of D ring by Heck reaction, wherein Y is O, $X_1$ is Ac, $X_2$ is Ms and $R_2$ is Boc, $X_3$, $X_4$, $R_1$ and $R_4$ are same as to the general formula 2.

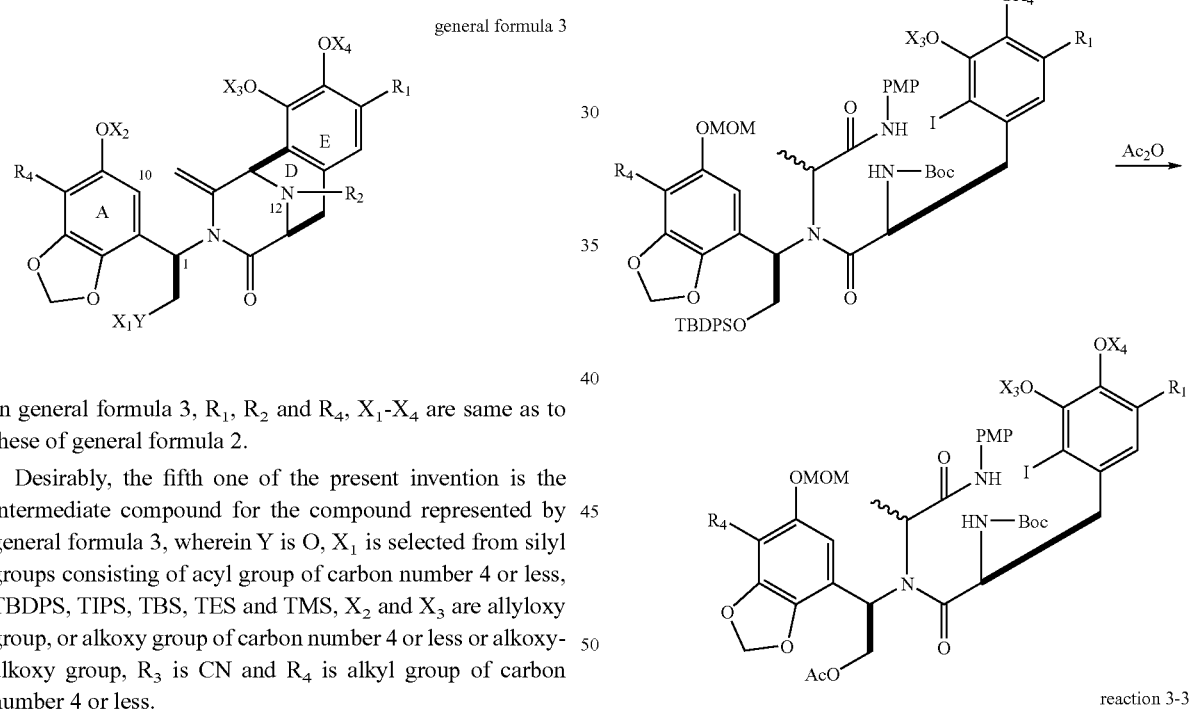

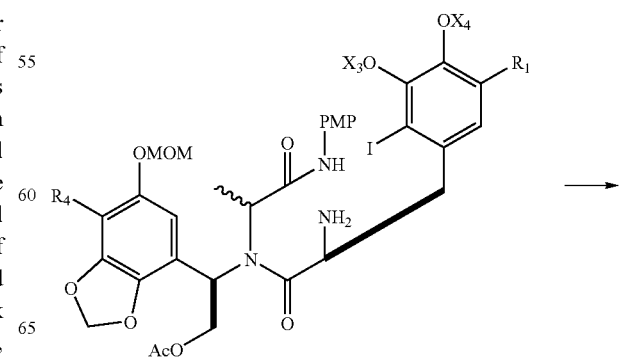

(Heck reaction)

The seventh one of the present invention is the amine compound which provides a segment to form a chemical structural site of A ring side of the intermediate compound of general formula 3 represented by general formula 4 by Ugi reaction.

general formula 4

In general formula 4, $R_4$, $X_2$, Y and $X_1$ is same as to these of general formula 2.

Desirably, the seventh one of the present invention is the amine compound, wherein Y is O, $X_1$ is selected from the group of silyl groups consisting of acyl group of carbon number 4 or less, TBDPS, TIPS, TBS, TES and TMS.

The eighth one of the present invention is a method for synthesis of the compound of general formula 4 consisting of the processes displayed by the reaction 2-1 which is the transforming reaction from $C_5$ hydroxyl group to methoxymethyl group, reaction 2-2 which is the introducing reaction of hydroxyl group to $C_{22}$, reaction 2-3 which is the Mannich reaction, reaction 2-4 which is the transforming reaction of $C_6$ hydroxyl group to trifloromethanesulfonyl group (Tf), reaction 2-5 which is the reducing reaction of lactone, reaction 2-6 which is the transforming reaction of $C_{22}$ hydroxyl to TBDPS group, reaction 2-7 which is the methylation reaction of $C_6$ Tfo group and reaction 2-8 which is the transforming reaction to amine, wherein Y=O, $X_1$ is TBOPS, $X_2$ is MOM and $R_4$ is Me.

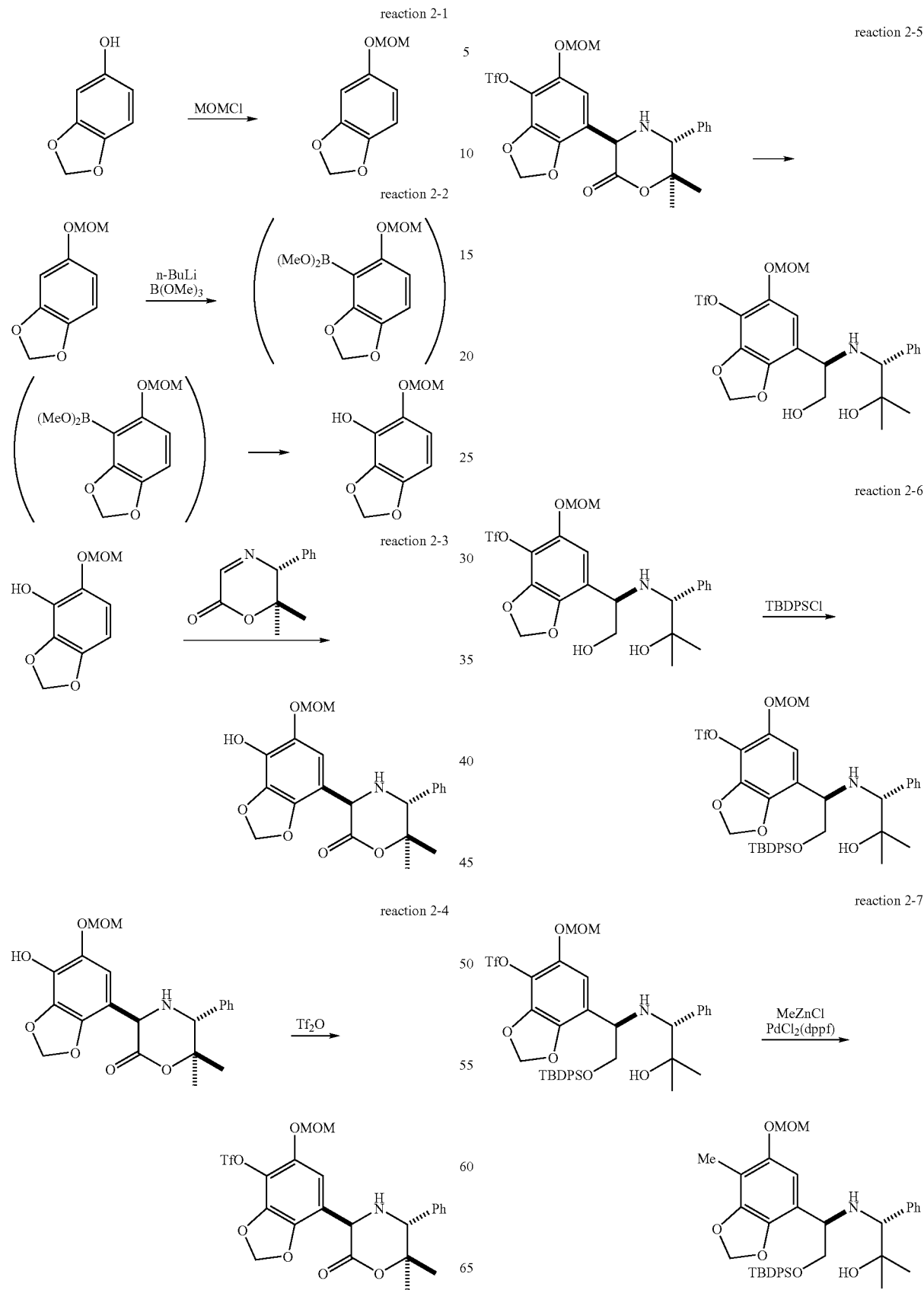

-continued

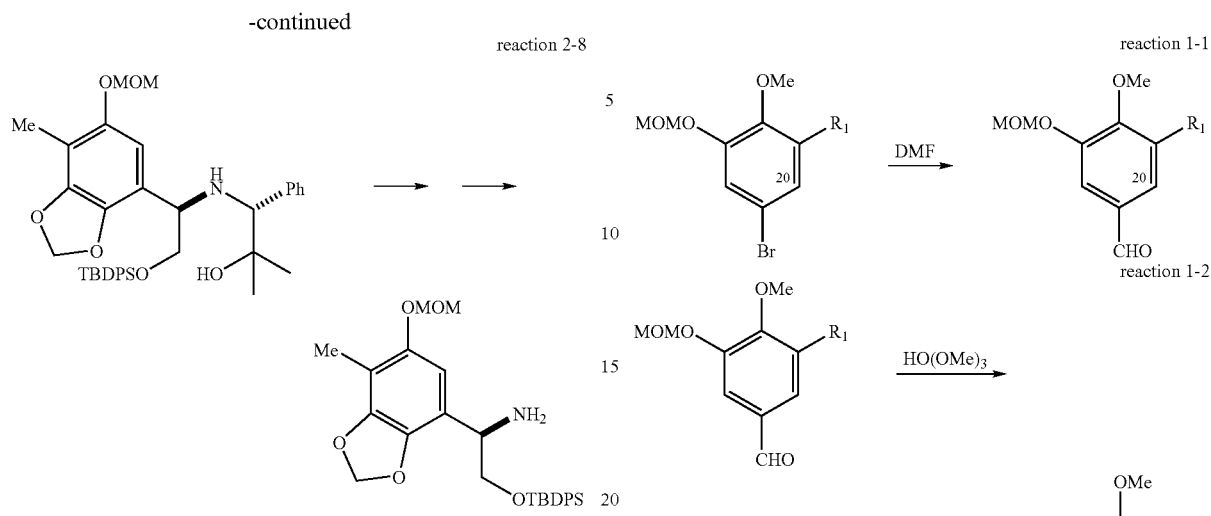

The ninth one of the present invention is the carboxylic acid compound which provides a segment forming a chemical structural site of E ring side of the intermediate compound of general formula 3 represented by general formula 5 by Ugi reaction.

general formula 5

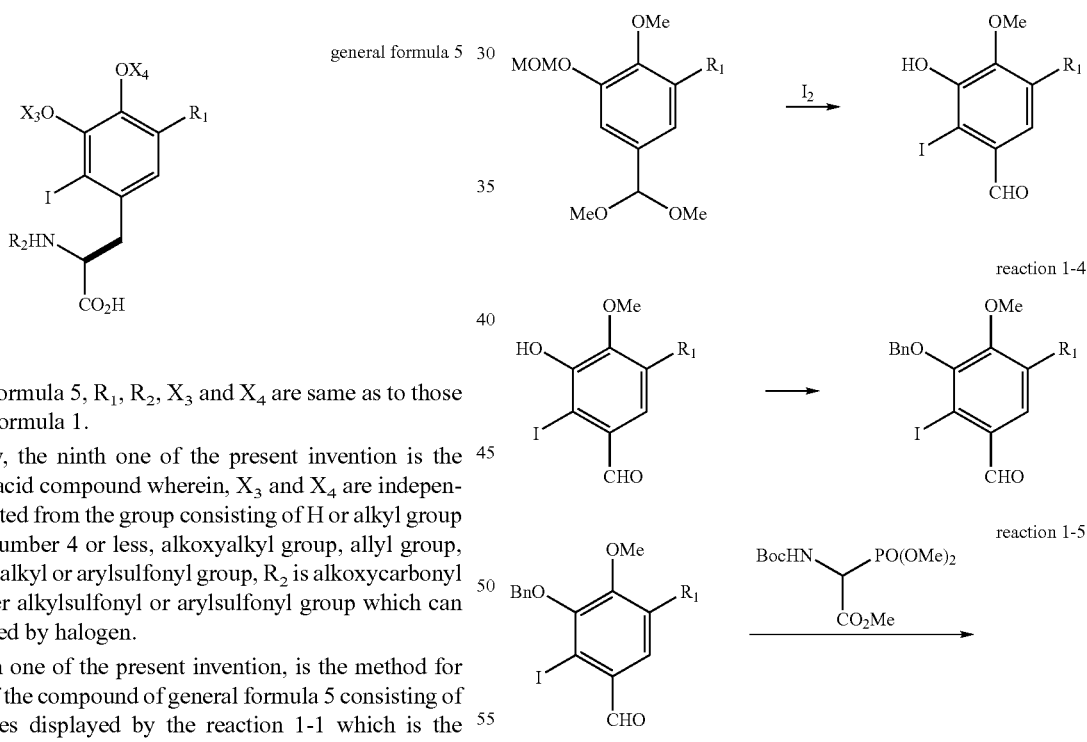

In general formula 5, $R_1$, $R_2$, $X_3$ and $X_4$ are same as to those of general formula 1.

Desirably, the ninth one of the present invention is the carboxylic acid compound wherein, $X_3$ and $X_4$ are independently selected from the group consisting of H or alkyl group of carbon number 4 or less, alkoxyalkyl group, allyl group, allyl group, alkyl or arylsulfonyl group, $R_2$ is alkoxycarbonyl group, lower alkylsulfonyl or arylsulfonyl group which can be substituted by halogen.

The tenth one of the present invention, is the method for synthesis of the compound of general formula 5 consisting of the processes displayed by the reaction 1-1 which is the introducing reaction of formyl group to $C_{20}$, the reaction 1-2 which is the transforming reaction of $C_{20}$ formyl group to dimethylacetal, the reaction 1-3 which is the iodination reaction of $C_{19}$ and acidic hydrolysis reaction, the reaction 1-4 which is the transforming reaction of $C_{18}$ hydroxyl group to benzyl group, the reaction 1-5 which is Honor-Emons reaction, reaction 1-6 which is the asymmetric reducing reaction by Duphos-Rh synthetic catalyst and reaction 1-7 which is the hydrolysis reaction of methylester, wherein $R_2$ is Boc, $X_3$ is Bn, $X_4$ is Me, ring and $R_1$ is same as to it of general formula 2.

-continued

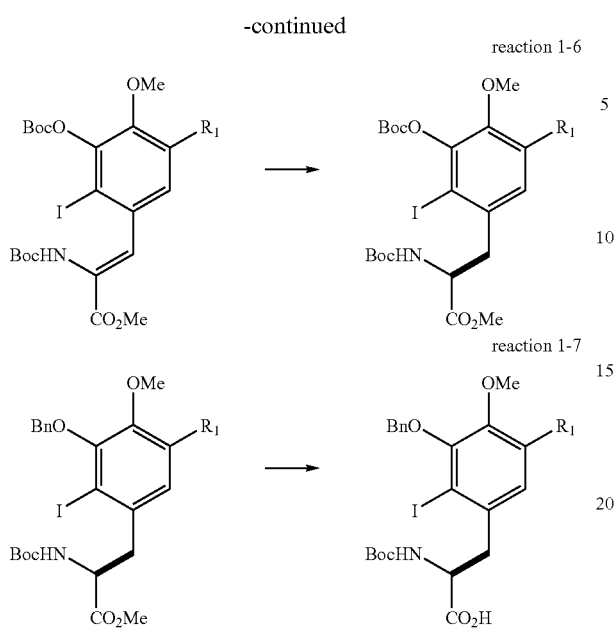

reaction 1-6 reaction 1-7

DESCRIPTION OF THE PREFERRED EMBODIMENT

The present invention will be illustrated more in detail according to the following description.

A. As mentioned above, the first feature of the present invention is the B ring forming reaction at ortho position of phenol which composes A ring to aldehyde indicated by reaction 4-9 process in synthesis process of the compound of the general formula 2. The feature of this reaction is that the reaction is progressed by a mild neutralized condition. Having OH group at the $C_4$ site which is expressed as the structural feature of the compound represented by general formula 2, the mild reaction condition is superior, since the compound disclosed in above mentioned prior art has hydrogen at this site, the reaction under harsh condition is required. Furthermore, from this synthesis intermediate, the synthesis of various analogous compounds is possible, and there is a possibility to obtain a compound having antineoplastic activity such as phtharasacidin being equal to Et 743.

B. The second feature of the present invention depends on utilizing the Ugi's 4 components condensation reaction of mentioned 3-1 reaction and Heck reaction of reaction 3-6 as the key process. First of all, in the Ugi's 4 components condensation reaction of 3-1, no condensation reagents is required for the generation of amide bond. The compound 3-1 make it possible to progress easily the formation of C ring of reaction 3-3. The ring forming reaction of reaction of 3-6 is not only the stereo chemistry of $C_3$ site controlled perfectly, but also can proceed the reaction using catalytic amount of $Pd_2(dba)_3$, which is an expensive reagent, by catalytic amount.

C. The third feature of the present invention is that the amine represented by general formula 4 and the carboxylic acid represented by general formula 5 can be provided by a large scale production.

D. The fourth feature of the present invention is the ring forming reaction of 10 members ring shown by reaction 5-3 process caused by bonding of sulfur atom at $C_4$ site.

The compound of the present invention, to the $C_4$ site of which a hydroxyl group is introduced, is possible to generate a cation of benzyl site easily under the acidic condition, therefore, the ring formation of 10 members ring by catching of sulfur atom to said cation is proceeded by high yield. When compared with the case which uses the compound whose $C_4$ site is H reported by Prof. E. J. Corey, the method of the present invention can use more mild condition. Therefore, the method of the present invention has the advantage for easily accomplishing of scale up, further has the possibility to introduce the ring of various numbers of member and is useful for the synthesis of various derivatives.

EXAMPLE

The present invention will be illustrated more in detail according to the specified Examples, however, these Examples are aimed at easily understanding the present invention and are not intended to limit the scope of the claim of the present invention.

Example 1

The synthesis of compound 2-8, wherein Y contained in general formula 4 is O, $X_1$ contained in general formula 4 is TBDPS, $X_2$ contained in general formula 4 is MOM and $R_4$ contained in general formula 4 is Me. The reaction process and the whole chemical formula of the generated compounds in each reaction process are shown by following synthesis process A.

Synthesis Process A;

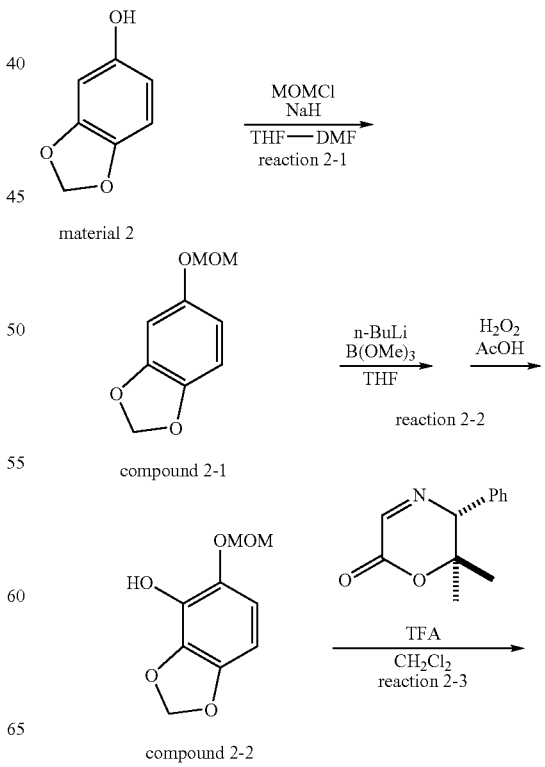

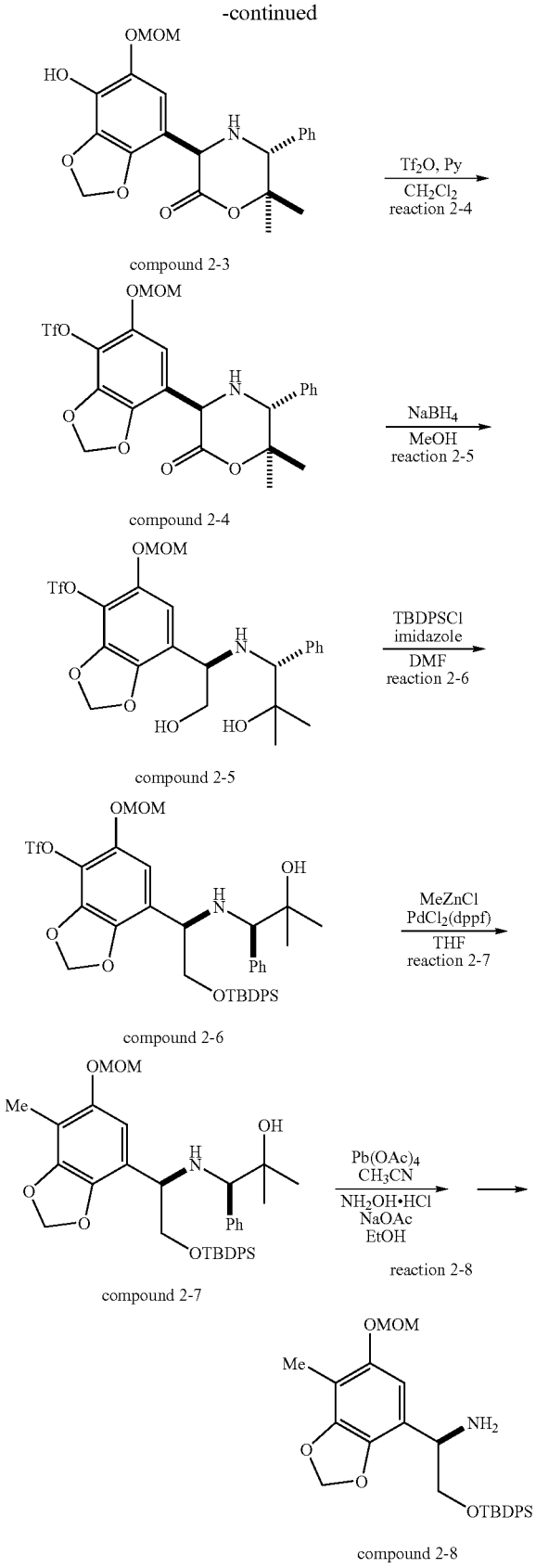

Detail of Synthetic Process A;

(1) Synthesis of Compound 2-1

NaH (40 g, 1.0 mol) was dispersed in 700 ml of the mixed solution of THF and DMF (5:2), THF solution (300 ml) of 3,4-methylenedioxyphenol (138 g, 1.0 mol) was dropped at 0° C. After stirred at room temperature for 30 minutes, MOMCl (84.5 g, 1.05 mol) was dropped and stirred at room temperature for 1 hour. Hexane and water were added to the reaction solution and the organic layer was separated. After the water layer was extracted by hexane, the organic layer was concentrated by vacuum. The residue was dissolved in hexane, washed by brine, then dried by $Na_2SO_4$.

After concentrated by vacuum, the residue was distilled by vacuum (103° C./0.35 mmHg), and the compound 2-1 (177 g, 0.97 mol, 97%) was obtained as a colorless oil. The physical property of compound 2-1 is shown in Table 1.

TABLE 1

| Compound 2-1 |
|---|
| IR(neat film)1244, 1215, 1176, 1153, 1099, 1069, 1040, 1004, 940, 922, 842, 813cm$^{-1}$; $^1$H NMR(400MHz, CDCl$_3$) δ 6.71(d, J=8.4Hz, 1H)6.63(s, 1H), 6.49(d, J=8.4Hz, 1H), 5.90(s, 2H), 5.08(s, 2H), 3.46(s, 3H); $^{13}$C NMR(100MHz, CDCl$_3$), δ 152.5, 148.1, 142.5, 108.4, 108.0, 101.2, 99.7, 95.4, 55.8. |

Synthesis of Compound 2-2

After n-BuLi (3.02 mol n-hexane solution, 11.0 ml, 33.2 mmol) was dropped in THF (100 ml) solution of compound 2-1 (5.44 g, 29.9 mmol) at 0C, the temperature was elevated to room temperature. The reaction solution was cooled down to 0° C., B(OOMe)$_3$ (4.10 ml, 36.1 mmol) was added, then AcOH(3.4 ml, 59 mmol) and aqueous solution of 7% $H_2O_2$ (26 ml, 60 mmol) were added. The reaction solution was stirred for 4.5 hours at room temperature, saturated aqueous solution of $(NH_4)_2SO_4$ (100 ml) and saturated aqueous solution of $Na_2SO_3$ (100 ml) were added, and an organic layer was dried with $MgSO_4$ then concentrated by vacuum. The residue was purified by silica gel chromatography (70% EtOAc in n-haxane), and the compound 2-2 (5.42 g 27.3 mmol) was obtained as a colorless oil. The physical property of compound 2-2 is shown in Table 2.

TABLE 2

| Compound 2-2 |
|---|
| IR(neat film) 3439, 1652, 1493, 1292, 1245, 1157, 1044, 932, 791cm$^{-1}$; $^1$H NMR(400MHz, CDCl$_3$) δ 6.55(d, J=8.4Hz, 1H), 6.45(br, 1H), 6.32(d, J=8.4Hz, 1H), 5.94(s, 2H), 5.09(s, 2H), 3.50(s, 3H); $^{13}$C NMR(100MHz, CDCl$_3$) δ 144.3, 141.3, 134.4, 132.0, 109.2, 101.6, 99.1, 97.3, 60.4, 56.3 |

Synthesis of Compound 2-3

As the method for synthesis of agent lactone (agent-1) which is added in the reaction 2-3, document, for example, ["Synthesis of Optically Active α-Arylglycines; Stereoselective Mannich Reaction of Phenols with a New Chiral template," S. Tohma, A. Endo, T. Kan, T. Fukuyama, Synlett, 1179-1199 (2001).] can be mentioned.

In $CH_2Cl_2$ (200 ml) solution of the compound 2-2 (19.8 g, 100 mmol) and agent-1 (20.3 g, 100 mmol), TFA (38 ml, 0.49 mol, 5 equiv) was dropped by 1.5 hours at −10° C. After the reaction solution was stirred for 40 minutes at room temperature, $Na_2CO_3$ (40 g, 0.38 mol, 3.8 equivalent) and $H_2O$ (200 ml) were added and extracted by $CH_2Cl_2$. The water layer was extracted by CH$_2$Cl$_2$, then the organic layer was washed by brine, dried by Na$_2$SO$_4$ and concentrated by CH$_2$Cl$_2$. The residue was purified by silica gel chromatography (30% EtOAc in n-haxane), and the compound 2-3 (35.6 g 89 mmol, 89%) was obtained a colorless oil. The physical property of compound 2-3 is shown in Table 3.

TABLE 3

Compound 2-3

[α]D$^{27}$ −75.2° (c=1.65, CHCl$_3$); IR(neat film)3327, 1724, 1506, 1457, 1299, 1151, 1118, 1082, 1049, 1101, 934cm$^{-1}$; $^1$H NMR(400 MHz, CDCl$_3$) δ 7.29-7.37(m, 5H), 6.51(s, 1H)5.93(s, 1h), 5.91(d, J=8.0Hz, 1H), 5.05(d, J=8.0Hz, 1H), 5.03(s, 1H)4.15(s, 1H), 3.51(s, 3H), 2.03(br, 1H), 1.37(s, 6H); $^{13}$C NMR(100MHz, CDCl$_3$) δ 169.0, 141.8, 141.4, 138.2, 134.8, 132.4, 128.4, 128.3, 128.3, 111.6, 110.0, 101.9, 86.7, 61.0, 57.1, 56.4, 26.6, 22.0;

Synthesis of Compound 2-4

To the solution of the compound 2-3 (242 mg, 0.603 mmol) and pyridine (0.15 ml, 1.9 mmol), Tf$_2$O (0.13 ml, 0.77 mmol, 1.3 equivalent) was dropped at 0° C. After the reacted product was stirred for 5 minutes, the aqueous solution of saturated NaHCO$_3$ was added and extracted by EtOAc. The organic layer was washed by the aqueous solution of 1N HCl and the saturated aqueous solution of NaHCO$_3$, then dried by MgSO$_4$ and concentrated by vacuum. The residue was purified by silica gel chromatography (in 50% EtOAc n-hexane), and the compound 2-4 (290 mg, 0.544 mmol, 90%) was obtained as a colorless oil. The physical properties of the compound 2-4 are shown in Table 4.

TABLE 4

Compound 2-4

[α]D$^{26}$ −32.1° (c=2.59, CHCl$_3$); IR(neat film)3333, 1733, 1496, 1462, 1427, 1299, 1216, 1138, 1056, 999, 979, 936, 832cm$^{-1}$; $^1$H NMR(400MHz, CDCl$_3$) δ 7.32-7.40(m, 5H), 6.71(s, 1H)6.06(s, 1H), 6.03(s, 1H), 5.19(d, J=5.8Hz, 1H), 5.14(d, J=5.8Hz, 1H), 5.09(s, 1H)4.23(s, 1H), 3.49(s, 3H), 2.01(br, 1H), 1.40(s, 6H); $^{13}$C NMR(100MHz, CDCl$_3$) δ 167.8, 144.9, 141.2, 140.2, 137.8, 128.3, 128.2, 128.1, 123.1, 120.2, 116.7, 108.0, 103.1, 95.9, 86.7, 61.3, 56.9, 56.3, 26.4, 21.8

Synthesis of Compound 2-5

To the MeOH (50 ml) solution of the compound 2-4 (4.70 g, 8.8 mmol), NaBH4 was added at 0° C. and stirred for 30 minutes. To the reaction solution, EtOAc (300 ml) was added and washed by 1N HCl (100 ml). The organic layer was washed by saturated aqueous solution of NaHCO$_3$, and after dried by MgSO$_4$, concentrated by vacuum. The residue was purified by silica gel chromatography (in 60% EtOAc n-hexane), and the compound 2-5 (4.04 g, 7.5 mmol, 85%) was obtained as a colorless oil. The physical properties of the compound 2-5 are shown in Table 5.

TABLE 5

Compound 2-5

[α]D$^{27}$ −102° (c=1.67, CHCl$_3$); IR(neat film)3398, 1497, 1456, 1426, 1218, 1136, 1054, 937, 833cm$^{-1}$; 1H NMR(400MHz, CDCl$_3$) δ 7.25-7.33(m, 5H), 6.63(s, 1H)5.94(s, 1H), 5.93(s, 1H), 5.11(d, J=6.8Hz, 1H), 5.07(d, J=6.8Hz, 1H), 3.65(br, 1H), 3.52-3.64(br, 2H), 3.50(s, 3H), 3.39(s, 1H), 2.71(br, 1H), TABLE 5-continued Compound 2-5

1.11(s, 6H); $^{13}$C NMR(100MHz, CDCl$_3$) δ 144.8, 141.6, 139.9, 139.2, 128.7, 128.1, 127.5, 122.4, 120.9, 120.1, 116.9, 107.1, 102.9, 95.6, 72.7, 68.9, 64.9, 56.9, 56.3, 27.9, 23.8;

Synthesis of Compound 2-6

To DMF solution of the compound 2-5 (1.00 g, 1.86 mmol) and imidazole (0.63 g, 9.3 mmol), TBDPSCl (1.22 ml, 4.7 mmol) was added and stirred at room temperature. To the reacted product, Et$_2$O and water were added and the organic layer was washed by brine, dried by Na$_2$SO$_4$ and concentrated by vacuum. The residue was purified by silica gel chromatography (in 10% EtOAc n-hexane), and the compound 2-6 (1.31 g, 1.69 mmol, 91%) was obtained as a colorless oil. The physical properties of the compound 2-6 are shown in Table 6.

TABLE 6

Compound 2-6

[α]D$^{27}$ −75.2° (c=1.65, CHCl$_3$); IR(neat film)3445, 1469, 1428, 1363, 1263, 1109, 1062, 991, 944, 826cm$^{-1}$; 1H NMR(400MHz, CDCl$_3$) δ 7.61(d, J=8.0Hz, 2H), 7.56(d, J=8.0Hz, 2H), 7.23-7.42(m, 11H), 6.62(s, 1H), 5.83(s, 2H), 5.10(d, J=6.8Hz, 1H), 5.08(d, J=6.8Hz, 1H), 3.77(dd, J=6.0, 6.8Hz, 1H), 3.67(m, 2H), 3.47(s, 3H), 3.37(s, 1H), 3.34(br, 1H), 1.909(s, 6H), 1.08(s, 9H); $^{13}$C NMR(100MHz, CDCl$_3$) δ 144.7, 141.8, 139.8, 139.5, 135.6, 132.9, 129.7, 128.5, 128.1, 127.7, 127.6, 127.4, 122.5, 121.0, 120.1, 116.9, 107.7, 102.7, 95.8, 72.2, 68.6, 66.4, 56.8, 56.3, 27.4, 26.8, 24.2, 19.2;

Synthesis of Compound 2-7

To the THF (105 ml) solution of the compound 2-6 (16.7 g, 21.5 mmol), MeZnCl (2.0M in THF solution, 37.5 ml, 75.1 mmol) was added at 0° C. After the temperature of the reaction solution was elevated to room temperature, PdCl$_2$ (dppf) (314 mg, 0.43 mmol) was added and refluxed by heating for 13.5 hours. EtOAc was added to the reaction solution, then washed by 1N HCl aqueous solution, saturated aqueous solution of NaHCO$_3$ and brine. The organic layer was dried by Na$_2$SO$_4$ and concentrated by vacuum. The residue was purified by silica gel chromatography (in 10% EtOAc n-hexane), and the compound 2-7 (13.4 g, 20.9 mmol, 97%) was obtained as a white solid. The physical properties of the compound 2-7 are shown in Table 7.

TABLE 7

Compound 2-7

[α]D$^{26}$−99.3° (c=0.81, CHCl$_3$); IR(neat film)3457, 2931, 1494, 1457, 1427, 1362, 1216, 1139, 1110, 1056, 1006, 936, 828cm$^{-1}$; 1H NMR(400MHz, CDCl$_3$ δ 7.63(d, J=6.8Hz, 2H), 7.56, (d, J=6.8Hz, 2H), 7.22-7.47(m, 11H), 6.30(s, 1H), 5.77(s, 2H), 5.03(d, J=5.6Hz, 1H), 5.01(d, J=5.6Hz, 1H), 3.83(dd, J=10.8, 10.8, 1H), 3.61-3.66(m, 2H), 3.44(s, 3H), 3.38(s, 1H), 2.08(s, 3H), 1.09(s, 9H), 1.06(s, 6H); $^{13}$C NMR(100MHz, CDCl$_3$) δ 150.8, 146.6, 140.0, 139.7, 135.6, 135.6, 133.2, 133.1, 130.9, 130.4, 130.0, 129.7, 129.6, 128.5, 128.4, 128.0, 127.7, 127.6, 127.2, 117.7, 109.6, 107.0, 100.8, 95.6, 72.1, 68.5, 66.6, 57.7, 56.0, 27.3, 26.8, 24.0, 19.2, 8.8

Synthesis of Compound 2-8

To the CH$_3$CN (12 ml) solution of the compound 2-7 (640 mg, 1.0 mmol), Pb(OAc)$_4$ (0.56 g, 1.26 mmol) was added slowly at 0° C. To the reaction solution, saturated aqueous solution of NaHCO$_3$ was added and extracted by EtOAc. The organic layer was washed by brine, dried by Na$_2$SO$_4$, concentrated by vacuum and crude product was obtained. The obtained crude product was dissolved in EtOH (10 ml), then hydrochloric acid salt of hydroxyl amine (347 mg, 5.6 mmol) and sodium acetate (410 mg, 5.0 mmol) were added at room temperature and stirred for 1.5 hours. EtOAc was added to the reaction solution, then filtrated by celite and concentrated by vacuum. The residue was dissolved with EtOAc and washed by 1N HCl aqueous solution, saturated aqueous solution of $NaHCO_3$ and brine. After the organic layer was dried by $Na_2SO_4$, concentrated by vacuum. The residue was purified by silica gel chromatography (EtOAc), and the compound 2-8 (436 mg, 0.88 mmol, 89%) was obtained. The physical properties of the compound 2-8 are shown in Table 8.

TABLE 8

Compound 2-8

$[\alpha]D^{23}$ –1.99° (c=1.30, $CHCl_3$); IR(neat film)1440, 1115, 1062, 991, 938, 826$cm^{-1}$; $^1$H NMR(400MHz, $CDCl_3$) δ 7.61-7.65(m, 4H), 7.35-7.45(m, 6H), 6.57(s, 1H), 5.81(s, 2H), 5.09(s, 2H), 4.16(dd, J=6.8, 4.8Hz, 1H), 3.87(dd, J=10.0, 4.8Hz, 1H), 3.76(dd, J=10.0, 6.8Hz, 1H), 3.48(s, 3H), 2.14(s, 3H), 1.08(s, 9H); $^{13}$C NMR(100MHz, $CDCl_3$) δ 150.8, 146.1, 139.1, 135.5, 135.5, 133.4, 133.3, 129.5, 129.5, 127.5, 120.7, 109.1, 105.8, 100.7, 95.7, 68.1, 55.9, 53.4, 26.7, 19.1, 8.8

Example 2

Synthesis of the Compound 1-7 Contained in General Formula 5

The process for synthetic reaction and the chemical structure of the products obtained at each process are totally shown in following synthesis process B.

Synthesis process B;

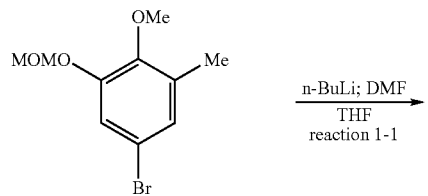

material-1

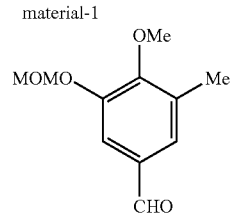

compound 1-1

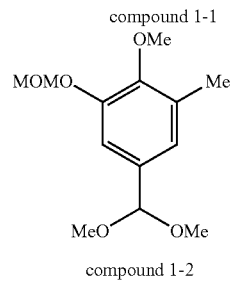

compound 1-2

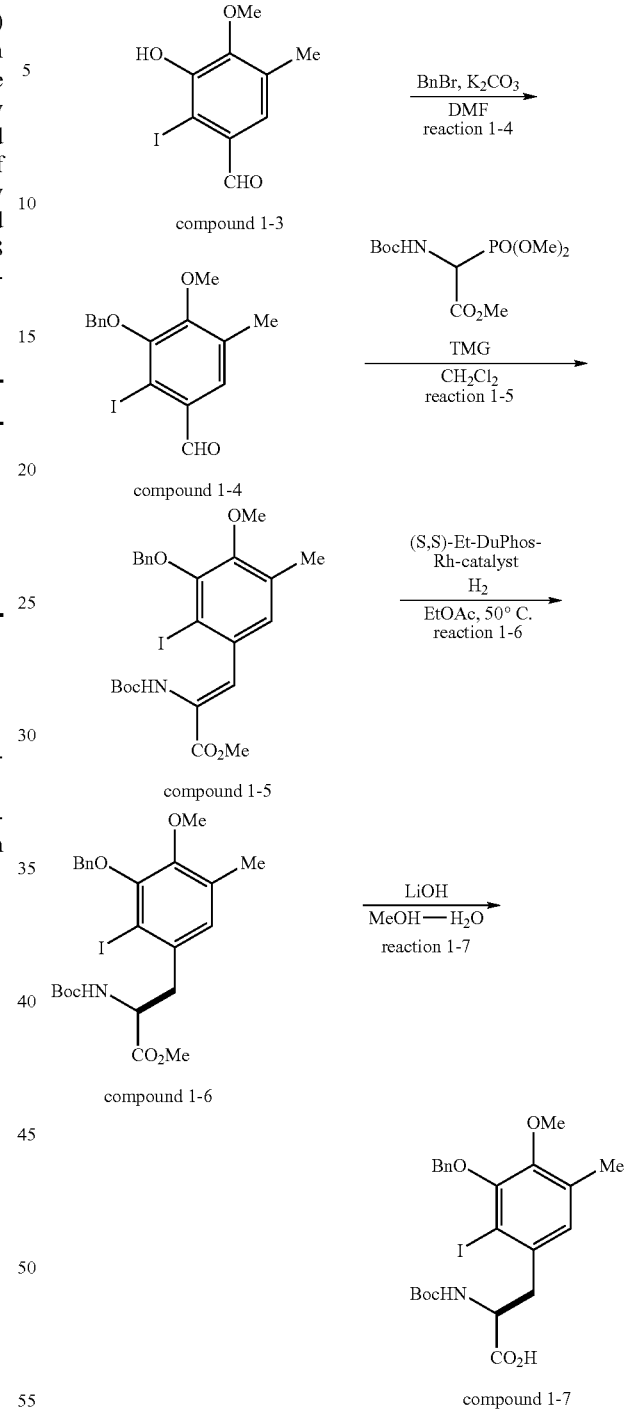

Detail of Synthesis of the Compound 1-7

Regarding the synthesis of bromide (starting material-1), for example, document of ["Synthetic Study on Ectenascidin 743 starting from D-glucose" A. Entoh, T. Kan, and T. Fukuyama, Synlett, 1103-1105 (1999)] can be mentioned.

Synthesis of compound 1-1

To the THF solution (900 ml) of the starting material-1 (114 g, 437 mmol), n-BuLi (2.46M in n-hexane solution, 270 ml, 664 mmol) was added at –78° C., then DMF (170 ml, 2.20 mol) was added. The temperature of the reaction solution was elevated to room temperature, and water was added to the reaction solution, then concentrated by vacuum. Et$_2$O was added to the residue, and washed by saturated aqueous solution of NaHCO$_3$ and brine. After dried by MgSO$_4$, concentrated by vacuum. The residue was purified by silica gel chromatography (30% Et$_2$O in n-hexane), and the compound 1-1 (73.0 g, 347 mmol, 79%) was obtained as a colorless oil. The physical properties of the compound 1-1 are shown in Table 9.

TABLE 9

Compound 1-1

IR(neat film)1699, 1585, 1488, 1451, 1382, 1299, 1235, 1155, 1133, 1099, 1051, 1003, 928, 863cm$^{-1}$; $^1$H NMR(400MHz, CDCl$_3$) δ 9.83(s, 1H), 7.49(s, 1H), 7.36(s, 1H), 5.25(s, 2H), 3.90(s, 3H), 3.51(s, 3H), 2.31(s, 3H); $^{13}$C NMR(100MHz, CDCl$_3$) δ 191.2, 153.5, 150.5, 132.8, 132.1, 126.9, 114.2, 95.0, 60.3, 56.3, 16.0

Synthesis of Compound 1-2

To the MeOH solution (5.0 ml) of the compound 1-1 (331 mg, 1.57 mmol) and CH(OMe)$_3$ (1.0 ml, 9.14 mol), CSA (20.2 mg, 0.09 mmol) was added and refluxed by heating for 1 hour. K$_2$CO$_3$ (103 mg, 0.75 mmol) was added to the reaction solution and concentrated by vacuum. The residue was dissolved in Et$_2$O and filtrated by a column of -basic alumina. After concentrated by vacuum, the compound 1-2 (381 mg, 1.49 mmol, 94%) was obtained as a colorless oil. The obtained compound 1-2 was used to the next reaction without refining. The physical properties of the compound 1-2 are shown in Table 10.

TABLE 10

Compound 1-2

1H NMR(400MHz, CDCl$_3$) δ 7.05(s, 1H), 6.93(s, 1H), 5.27(s, 1H), 5.25(s, 2H), 3.89(s, 3H), 3.59(s, 3H), 3.34(s, 3H), 2.32(s, 3H)

Synthesis of Compound 1-3

To the Et$_2$O solution (4.0 ml) of the compound 1-2 (381 mg, 1.49 mmol), n-BuLi (2.46M in n-hexane solution, 0.95 ml, 2.34 mmol) was added at 0° C., then the temperature was elevated to room temperature. After reduced the temperature of the reaction solution to 0° C., Et$_2$O (3.0 ml) solution of I$_2$ (648 mg, 2.55 ml) was added. After water and saturated aqueous solution of NaHCO$_3$ were added, extracted by EtOAc. The organic layer was washed by brine, dried by MgSO$_4$ and concentrated by vacuum. The residue was dissolved by THF (5.0 ml) and 12N HCl (2.0 ml) aqueous solution was added at room temperature. After stirred for 15 minutes, neutralized by saturated aqueous solution of NaHCO$_3$ and extracted by EtOAc. The organic layer was washed by saturated aqueous solution of brine, dried by MgSO$_4$ and concentrated. The residue was dissolved by CH$_2$Cl$_2$ and filtrated by silica gel and concentrated by vacuum. The obtained solid was washed by n-hexane and the compound 1-3 (314 mg, 1.07 mmol, 72%), and the compound 1-3 was obtained as a colorless solid. The physical properties of the compound 1-3 are shown in Table 11.

TABLE 11

Compound 1-3

IR(neat film)3389, 1670, 1583, 1464, 1412, 1299, 1247, 1127, 997cm$^{-1}$; $^1$H NMR 400MHz, CDCl$_3$) δ 10.0(s, 1H), 7.37(s, 1H), 6.43(bs, 1H), 3.89(s, 3H), 2.32(s, 3H); $^{13}$C NMR(100MHz, CDCl$_3$) δ 194.9, 149.9, 149.2, 131.3, 130.9, 125.3, 125.3, 60.8, 15.8;

The Synthesis of Compound 1-4

To the CH$_3$CN (3.0 ml) solution of the compound 1-3 (325 mg, 1,11 mmol) and K$_2$CO$_3$ (465 mg, 3.37 mmol) BuBr (140 μl, 1.18 mmol) were added at room temperature and refluxed by heating for 40%. After CH$_2$Cl$_2$ were added to the reaction solution, filtrated by Celite, then concentrated by vacuum. The residue was purified by silica gel chromatography (50% CH$_2$Cl$_2$ in n-hexane), and the compound 1-4 (415 mg, 1.09 mmol, 98%) was obtained as a colorless oil. The physical properties of the compound 1-4 are shown in Table 12.

TABLE 12

Compound 1-4

IR(neat film)1684, 1576, 1464, 1303, 1153, 1068, 1005cm$^{-1}$; $^1$H NMR (400MHz, CDCl$_3$) δ 10.0(s, 1H), 7.60(d, 8.0Hz, 2H), 7.59(s, 1H), 7.30-7.45(m, 3H), 5.01(s, 2H), 3.93(s, 3H), 2.30(s, 3H); $^{13}$C NMR (100MHz, CDCl$_3$) δ 195.3, 157.1, 151.3, 136.3, 133.3, 131.3, 128.7, 128.5, 128.4, 128.2, 98.2, 74.9, 60.6, 15.7;

The Synthesis of Compound 1-5

To the CH$_2$Cl$_2$ solution (100 ml) of the compound 1-4 (8.30 g, 21.7 mmol) and methyl-2-butoxycarbonylamino-dimethylsulfonoacetate (7.76 g, 26.1 mmol), TMG (4.10 ml, 32.7 mmol) was added at room temperature and stirred for 24 hours at room temperature. The reaction solution was washed by 10% citric acid and saturated aqueous solution of NaHCO$_3$, then the organic layer was dried by MgSO$_4$ and concentrated by vacuum. The residue was purified by silica gel chromatography, and the compound 1-5 (11.2 g, 20.2 mmol, 1.93%) was obtained as a yellow crystal. The further refining was carried out by re-crystallization (EtOAc/n-hexane). The physical properties of the compound 1-5 are shown in Table 13.

TABLE 13

Compound 1-5

IR(neat film)3336, 1717, 11457, 1367, 1249, 1160, 1065, 1003cm$^{-1}$; $^1$H NMR(400MHz, CDCl$_3$) δ 7.60(d, J=6.8Hz, 2H), 7.36-7.60(m, 3H), 7.24(s, 1H), 7.20(s, 1H), 5.00(s, 2H), 3.88(s, 3H), 3.86(s, 3H), 2.23 (s, 3H); $^{13}$C NMR(100MHz, CDCl$_3$) δ 165.6, 152.4, 151.6, 136.8, 134.2, 132.5, 131.7, 128.7, 128.4, 128.2, 126.8, 125.4, 96.9, 80.9, 74.6, 60.5, 52.7, 28.0, 15.8

The Synthesis of Compound 1-6

The EtOAC solution (30 ml) of frozen and degased compound 1-5 (5.04 g, 9.10 mmol) and Rh [(COD)-(S,S)-Et-DuPHOS]$^+$TfO— (99.0 mg, 0.14 mmol, 1.5 mol %) was poured into a high pressure reactor and stirred for 22 hours under hydrogen atmosphere of 500 atm at 50° C. The reaction solution was concentrated by vacuum and the residue was purified by silica gel chromatography (50% EtOAc in n-hexane), and the compound 1-6 (5.01 g, 902 mmol, 99%) was obtained as a light yellow crystal. Wherein, (S,S)-Et-DuPhos-catalyst Rh{[(COD)-(S,S)-Et-DuPHOS]$^+$TfO—} is shown as follows.

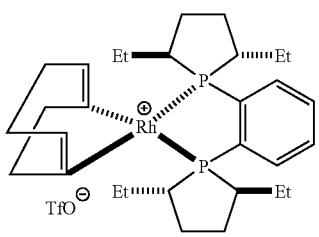

The physical properties of the compound 1-6 are shown in Table 14.

TABLE 14

Compound 1-6

[α]$_D^{27}$+7.4° (c=1.09, CHCl$_3$); R(neat film)3374, 1764, 1711, 1510, 12457, 1363, 1162, 1068, 1003cm$^{-1}$; $^1$H NMR(400MHz, CDCl$_3$) δ 7.60(d, J=8.8Hz, 2H), 7.32-7.45(m, 3H), 6.85(s, 1H), 5.06(d, J=8.8Hz, 1H), 4.99(s, 1H), 4.62(ddd, J=9.2, 8.8, 5.6Hz, 1H), 3.82(s, 3H), 3.72(s, 3H), 3.28(dd, J=14.4, 5.6Hz, 1H), 3.09(dd, J=14.4, 9.2Hz, 1H), 2.23(s, 3H), 1.43(s, 9H); $^{13}$C NMR (100MHz, CDCl$_3$) δ 172.4, 154.9, 151.7, 150.4, 136.9, 135.4, 132.3, 128.6, 128.4, 128.1, 127.8, 97.0, 79.8, 74.5, 60.4, 53.8, 52.3, 42.7, 28.2, 15.6;

The Synthesis of Compound 1-7

LiOH (750 mg, 17.9 mmol, 2.0 equivalent) was added to the mixed solution of compound 1-6 (5.01 g, 9.02 mmol) in MeOH (40 ml), H$_2$O (10 ml) and THF (10 ml) at 0° C. Benzene was added to the reaction solution and concentrated by vacuum. 10% of aqueous solution of citric acid was added to the residue and extracted by EtOAc. Organic layer was washed by brine and dried by MgSO$_4$ and concentrated by vacuum. Thus the compound 1-7 (4.90 g, 9.05 mmol, 100%) was obtained as a white solid. The physical property of the compound 1-7 is shown in Tale 15.

TABLE 15

Compound 1-7

[α]$_D^{27}$−14.1° (c=5.00, CHCl$_3$); IR(neat film)3309, 2560, 1716, 1497, 1471, 1404, 1368, 1307, 1243, 1163, 1063, 1008, 907, 845, 804cm$^{-1}$; 1H NMR(400MHz, CDCl$_3$) δ 7.61(br, 2H), 7.36-7.44(br, 3H), 6.90(s, 1H), 5.00(br, 2H), 4.63(br, 1H), 3.83(s, 3H), 3.43(br, 1H), 2.94-3.20(br, 1H), 2.25(s, 3H), 1.10-1.40(br, 9H); $^{13}$C NMR (100MHz, CDCl$_3$) δ 176.2, 175.4, 156.7, 155.2, 151.4, 150.4, 150.3, 136.9, 135.8, 135.3, 132.3, 132.2, 128.7, 128.6, 128.4, 128.4, 128.1, 127.9, 97.1, 96.7, 81.1, 80.1, 77.2, 74.5, 60.4, 60.3, 54.1, 53.8, 53.7, 44.6, 42.3, 42.2, 42.2, 28.2, 27.9, 15.6.

Example 3

The processes for synthesis of the compound 3-6 contained in general formula 3 and whole products in each process are shown in following synthetic process C.

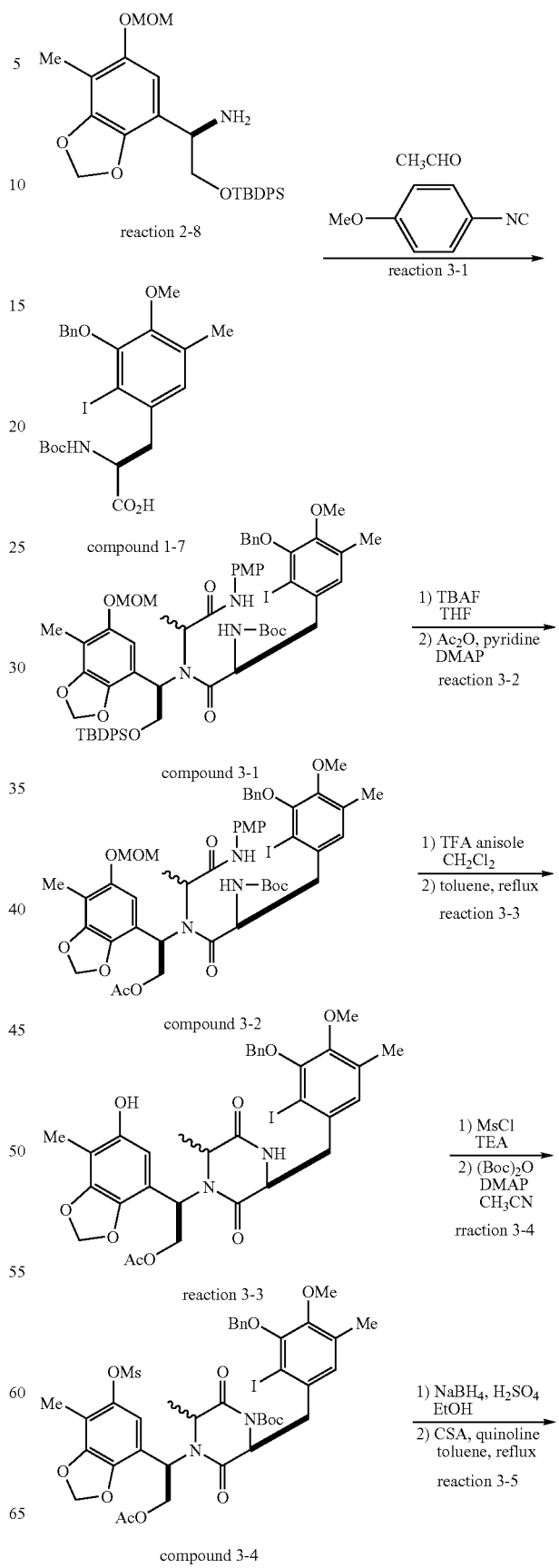

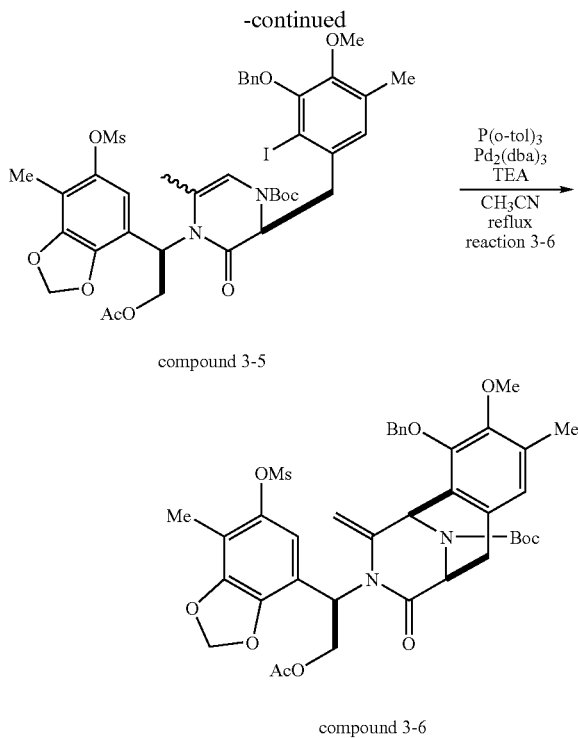

compound 3-5 compound 3-6

Detail of Synthesis of C;

Synthesis of Compound 3-1

To the MeOH solution (200 ml) of compound 2-8 (9.63 g, 19.5 mmol), compound 1-7 (10.57 g, 19.5 mmol) and p-methoxyphenylisocyanide (3.90 g, 29.3 mmol, 1.5 equivalent), acetoaldehyde (22 ml, 0.39 mol, 20 equivalent) was added at room temperature and refluxed for 1 hour. After concentrated by vacuum, residue was purified by silica gel chromatography (40% EtOAc, n-hexane) and compound 3-1 (21.02 g, 17.6 mmol, 90%) was obtained as a yellow solid. The physical properties of 3-1 are shown in Table 16.

TABLE 16

Compound 3-1

IR(neat film)3315, 1699, 1687, 1511, 1463, 1428, 1367, 1245, 1159, 1112, 1062, 826cm$^{-1}$; $^1$H NMR(400MHz, CDCl$_3$) δ 8.60-9.20(m, 1H), 7.25-7.75(m, 17H), 6.50-7.20(m, 4H), 4.80-5.85(m, 9H), 3.90-4.80(m, 3H), 3.60-3.85(m, 6H), 3.40-3.50(m, 3H), 2.90-3.50(m, 2H), 1.85-2.25(m, 6H), 0.75-1.50(m, 21H); $^{13}$C NMR(100MHz, CDCl$_3$) δ 173.4, 172.0, 171.3, 170.1, 168.7, 167.9, 156.2, 156.1, 155.9, 155.6, 155.3, 154.3, 151.5, 151.4, 151.3, 151.0, 150.9, 150.8, 150.5, 150.1, 150.0, 146.9, 146.5, 139.8, 139.7, 136.8, 136.7, 136.6, 136.5, 135.6, 135.5, 135.4, 135.3, 135.2, 132.6, 132.5, 132.4, 132.2, 132.1, 132.0, 131.6, 131.1, 131.0, 129.9, 129.7, 129.6, 129.3, 128.5, 128.4, 128.3, 128.2, 128.0, 127.9, 127.7, 127.5, 127.4, 127.3, 123.0, 121.7, 121.5, 120.5, 113.7, 113.5, 113.4, 113.3, 113.1, 110.9, 106.2, 106.0, 100.9, 100.6, 97.5, 96.7, 96.6, 96.2, 95.8, 95.5, 95.3, 80.6, 80.5, 80.3, 79.3, 79.0, 74.4, 74.3, 71.5, 70.4, 62.6, 62.5, 60.2, 60.1, 59.7, 57.2, 56.2, 56.1, 55.9, 55.1, 54.5, 54.4, 51.5, 51.3, 42.9, 41.8, 41.1, 41.1, 28.1, 28.0, 27.9, 27.8, 27.1, 27.0, 26.9, 26.4, 19.1, 19.0, 18.9, 17.8, 17.1, 15.4, 15.3, 15.2, 15.1, 14.9, 14.8, 8.8 8.7, 8.5;

Synthesis of Compound 3-2

TBAF (1M THF solution, 20 ml, 20.0 mmol) was added to THF solution (200 ml) of compound 3-1 (21.02 g, 17.6 mmol) was added at room temperature and stirred for 30 minutes.

The mixed solvent of EtOH and n-hexane (3:7) was added and concentrated by vacuum. The residue was purified by silica gel chromatography (EtOAc) and yellow solid (14.90 g, 15.6 mmol, 89%) was obtained. DMPA (97 mg, 0.79 mmol) was added to the mixed solution of acetic anhydride (30 ml) of alcohol (14.90 g, 15.6 mmol) and pyridine (60 ml) and stirred for 30 minutes at 50° C. After concentrated by vacuum, residue was purified by silica gel chromatography (60%, EtOAc n-hexane) and the compound 3-2 (14.54 g, 14.6 mmol, 93%) was obtained as yellow solid. The physical properties of compound 3-2 are shown in Table 17.

TABLE 17

Compound 3-2

IR(neat film)3318, 1743, 1700, 1511, 1436, 1368, 1304, 1245, 1170, 1112, 1060, 830cm$^{-1}$; $^1$H NMR(400MHz, CDCl$_3$) δ 8.90-9.30(m, 1H), 7.55(d, J=6.8Hz, 2H), 7.20-7.50(m, 5H), 6.30-7.20(m, 2H), 6.80(d, J=6.8Hz, 2H), 5.84-5.88(br, 2H), 5.60-5.80(m, 2H), 5.20-5.45(m, 2H), 5.00-5.20(m, 2H), 4.93-4.97(m, 2H), 4.70-4.90(m, 1H), 4.40-4.70(m, 1H), 3.65-3.80(m, 6H), 3.35-3.50(m, 3H), 2.90-3.35 M, 1H), 1.80-2.25(m, 9H), 1.10-1.55(m, 12H); $^{13}$C NMR(100MHz, CDCl$_3$) δ 173.6, 173.2, 172.7, 172.0, 170.1, 170.0, 169.7, 169.5, 169.5, 169.4, 168.2, 156.4, 156.1, 155.8, 155.2, 154.3, 151.5, 151.3, 151.2, 151.2, 151.1, 150.6, 150.3, 147.1, 146.8, 146.6, 140.0, 139.8, 139.3, 136.8, 136.7, 136.7, 136.5, 135.0, 134.9, 134.6, 132.5, 132.0, 131.1, 131.0, 128.8, 128.5, 128.4, 128.4, 128.3, 128.2, 128.1, 128.0, 127.9, 121.8, 121.8, 121.8, 121.6, 121.4, 121.2, 120.6, 113.9, 113.9, 113.8, 113.5, 113.1, 112.6, 112.1, 111.7, 111.3, 105.9, 105.7, 105.3, 101.1, 101.0, 100.7, 96.8, 96.5, 95.4, 95.1, 79.6, 79.1, 74.4, 70.6, 62.0, 60.3, 60.2, 57.3, 56.5, 56.2, 56.0, 55.8, 55.2, 50.6, 50.1, 43.5, 28.1, 28.0, 27.9, 27.8, 20.9, 20.7, 17.6, 15.3, 14.8, 8.8;

Synthesis of Compound 3-3

To the CH$_2$Cl$_2$ (290 ml) solution of compound 3-2 (14.5 g, 14.5 mmol) and anisole (79 ml, 0.73 mol), TFA (58 ml, 0.75 mol) was added at 0° C., then stirred at room temperature for 9 hours. 7% Na$_2$SO$_4$ aqueous solution was added to the reaction solution and extracted by EtOAc. The organic layer was washed by saturated aqueous solution of NaHCO$_3$ and by brine, dried by MgSO$_4$ and concentrated to 300 ml, then heat refluxed for 1 hour. The solvent was evaporated off by vacuum, and the residue was purified by column chromatography (in 70% EtOAc m-hexane). Thus the compound 3-3 (19.7 g, 27.0 mmol, 87%) was obtained as a brownish powder. The physical property of the compound 3-3 is shown in Table 18.

TABLE 18

Compound 3-3 minor isomer; IR(neat film)3345, 1752, 1683, 1652, 1456, 1306, 1232, 1093, 1037, 1007cm$^{-1}$; $^1$H NMR(400MHz, CDCl$_3$) δ 7.56(d, J=8.2, 2H), 7.38-7.41(m, 3H), 6.85(s, 1H), 6.23(s, 1H), 6.20(br, 1H), 5.89(s, 1H), 5.86(s, 1H), 5.70(dd, J=8.4, 7.2Hz, 1H), 4.95(s, 2H), 4.69(dd, J=11.0, 7.2Hz, 1H), 4.57(dd, J=11.0, 8.4Hz, 1H), 4.29(dd, J=9.3, 3.9Hz, 1H), 3.88(q, J=7.1Hz, 1H), 3.80(s, 3H), 3.46(dd, J=13.7, 3.9Hz, 1H), 3.21(dd, J=13.7, 9.3Hz, 1H), 2.21(s, 3H), 2.09(s, 3H), 2.05(s, 3H), 1.45(d, J=7.1Hz, 3H); $^{13}$C NMR(100MHz, CDCl$_3$) δ 170.7, 168.7, 166.5, 151.8, 150.0, 151.0, 147.0, 139.0, 136.7, 134.5, 133.2, 128.6, 128.4, 128.2, 128.1, 111.8, 109.1, 106.3, 100.9, 97.3, 74.6, 62.7, 60.4, 57.0, 55.0, 44.9, 21.2, 20.8, 15.5, 8.7;
major isomer; IR(neat film)3374, 1751, 1683, 1651, 1430, 1314, 1265, 1233, 1094, 1040, 1006cm$^{-1}$; $^1$H NMR(400MHz, CDCl$_3$) δ (d, J=8.3Hz, 2H), 7.36-7.43(m, 3H), 6.86(s, 1H), 6.40(s, 1H), 5.93(2, 1H), 5.92(s, 1H), 5.62(dd, J=8.9, 5.8Hz, 1H), 5.50 (s, 1H), 5.15(br, 1H), 5.03(d, J=6.8Hz, 1H), 5.021(d, J=6.8Hz, 1H), 4.76(dd, J=11.7, 8.9Hz, 1H), 4.60(dd, 11.7, 5.8Hz, 1H), 4.34(dd, J=10.7, 3.9Hz, 1H), 4.18(q, J=7.1Hz, TABLE 18-continued Compound 3-3

1H), 3.84(s, 3H), 3.81(dd, J=14.2, 3.9Hz, 1H), 2.84(dd,
J=14.2, 10.7Hz, 1H), 2.25(s, 3H), 2.13(s, 3H), 2.07(s, 3H),
1.15(d, J=7.1Hz, 1H); $^{13}$C MHz, CDCl$_3$) δ 170.7, 170.3, 166.9,
152.2, 151.0, 150.8, 146.8, 138.9, 136.6, 134.1, 133.4, 128.6,
128.4, 128.3, 128.2, 112.5, 108.9, 106.5, 101.0, 96.2, 74.6, 62.0,
60.4, 54.9, 53.3, 52.5, 41.5, 20.8, 18.0, 15.6, 8.7;

Synthesis of Compound 3-4

To the CH$_2$Cl$_2$ (100 ml) solution of compound 3-3 (19.3 g, 26.4 mmol) and trimethylamine (11.8 ml, 84.6 mmol), MsCl (2.60 ml, 33.8 mmol) was added at 0° C., then stirred for 1 hour. EtOAc (400 ml) was added to the reaction solution and washed by 1N HCl, saturated NaHCO$_3$ aqueous solution and brine, then dried by MgSO$_4$. After concentrated by vacuum, the residue was purified by silica gel chromatography (in 70% EtOAc m-hexane). Thus, the mecyl body (19.4 g, 24.0 mmol, 91%) was obtained as a yellow solid.

To the CH$_3$CN (15 ml) solution of mecyl body (3.00 g, 3.71 mmol) and (Boc)$_2$O (1.36 g, 6.22 mmol) was added and stirred for 6.5 hours. EtOAc was added to the reaction solution and washed with 0.5N HCl, saturated NaHCO$_3$ aqueous solution and brine. The organic layer was dried by MgSO$_4$, concentrated by vacuum and the residue was purified by silica gel chromatography (in 50% EtOAc n-hexane). Thus the compound 3-4 (3.27 g, 3.60 mmol, 97%) was obtained as a yellow solid. The physical property of the compound 3-4 is shown in Table 19.

TABLE 19

Compound 3-4 major isomer; IR(neat film)1775, 1733, 1670, 1455, 1429, 1368, 1308,
1285, 1244, 1172, 1148, 1066, 970, 937cm$^{-1}$; $^1$H NMR(400MHz, CDCl$_3$)
δ 7.58(d, J=6.8Hz, 2H), 7.33-7.41(m, 3H), 6.87(s, 1H), 6.82
(s, 1H), 5.97(s, 1H), 5.96(s, 1H), 5.56, (dd, J=8.0, 8.0Hz, 1H),
5.14(dd, J=8.0, 4.8Hz, 1H), 4.95(d, J=10.0Hz, 1H), 4.91
(d, J=10.0Hz, 1H), 4.63(dd, J=10.8, 8.0Hz, 1H), 4.56(dd,
J=10.8, 8.0Hz, 1H), 3.98(q, J=8.0, 1H), 3.78(s, 3H), 3.53
(dd, J=14.8, 4.8Hz, 1H), 3.23(dd, J=14.8, 8.0Hz, 1H), 3.16
(s, 3H), 2.20(s, 3H), 2.19(s, 3H), 2.03(s, 3H), 1.45(d,
J=8.0Hz, 3H); $^{13}$C NMR(100MHz, CDCl$_3$) δ 170.5, 167.8, 166.0,
151.8, 150.9, 149.5, 147.3, 144.1, 142.5, 136.8, 134.9, 132.9, 128.7,
128.4, 128.4, 128.2, 115.3, 115.1, 113.1, 102.1, 97.5, 84.4, 74.6, 62.0,
60.4, 59.5, 56.5, 56.5, 53.5, 44.6, 38.0, 27.8, 20.8, 20.8, 15.5, 9.9

Synthesis of Compound 3-5

To the EtOH (100 ml) and CH$_2$Cl$_2$ (10 ml) mixed solution of the compound 3-4 (4.11 g, 4.52 mmol), H$_2$SO$_4$ (3.0 ml, 9.0 mmol in 3.0M EtOH solution) and NaBH$_4$ (867 mg, 22.9 mmol) were added at 0° C. After acetone (10 ml) was added, neutralized by saturated NaHCO$_3$ aqueous solution, added EtOAc and filtrated by Cellite. Then concentrated by vacuum, EtOH was added to the residue and washed by saturated NaHCO$_3$ aqueous solution. The organic layer was dried by MgSO$_4$, concentrated by vacuum and aminal (4.19 g) was obtained. The obtained aminal is dissolved in toluene (40 ml), CSA (1.07 g, 4.61 mmol) and quinoline (0.82 ml, 7.0 mmol) are added and heat refluxed for 3 hours. EtOAc is added to the reaction solution and washed by 1N HCl aqueous solution, saturated NaHCO$_3$ aqueous solution and brine aqueous solution. The organic layer is dried by MgSO$_4$, concentrated by vacuum and the residue was purified by silica gel chromatography (in 50% EtOAc n-hexane). Thus the compound 3-5 (3.54 g, 3.97 mmol, 88%) was obtained as a yellow solid. The physical property of the compound 3-5 is shown in Table 20.

TABLE 20

Compound 3-5

[α]D$^{27}$+2.9° (c=2.97, CHCl$_3$); IR(neat film)1742, 1692,
1463, 1418, 1362, 1336, 1240, 1172, 1065, 1005, 962, 890, 805cm$^{-1}$;
$^1$H NMR(400MHz, CDCl$_3$) δ 7.60(d, J=6.8Hz, 2H),
7.36-7.44(m, 3H), 6.87(br, 1H), 6.69(s, 1H), 6.21(s, 1H),
6.01(s, 1H), 5.96(s, 1H), 4.97(s, 2H), 4.93(br, 1H), 4.85(br, 2H),
3.80(s, 3H), 3.19(s, 3H), 2.91(br, 2H), 2.22(s, 3H), 2.20(s, 3H),
2.04(s, 3H), 1.32(s, 9H); $^{13}$C NMR(100MHz, CDCl$_3$) δ 170.3, 151.5,
151.3, 151.1, 150.9, 150.1, 150.1, 150.1, 146.7, 143.1, 143.0, 142.2,
142.1, 136.7, 136.6, 135.8, 134.7, 134.7, 132.0, 131.5, 129.2, 129.1,
128.4, 128.2, 127.9, 127.9, 127.9, 127.7, 126.2, 121.3, 120.8, 115.4,
115.2, 114.0, 113.9, 101.7, 97.0, 96.5, 80.8, 80.7, 77.3, 77.2, 77.0,
76.7, 74.2, 62.4, 62.3, 60.1, 60.0, 57.2, 55.7, 39.1, 38.8, 37.4, 37.4,
27.8, 27.5, 20.4, 16.3, 15.2, 9.6;

Synthesis of Compound 3-6

Pd$_2$(dba)$_3$ (325 mg, 0.36 mmol, 5 mol %) was added to CH$_3$CN (50 ml) solution of the compound 3-5 (6.27 g, 7.02 mmol), P(o-tol)$_3$ (428 mg, 1.41 mmol, 0.2 equivalent) and triethylamine (4.0 ml, 29 mmol, 4.1 equivalent) and refluxed by heating for 2 hours. After EtOAc was added to the reaction solution and concentrated, EtOAc is added to the residue and washed by 10% citric acid, saturated NaHCO$_3$ aqueous solution and brine. The organic layer was dried by MgSO$_4$, concentrated by vacuum and the residue was purified by silica gel chromatography (in 50% EtOAc n-hexane). Thus the compound 3-6 (4.44 g, 5.81 mmol, 83%) was obtained as a yellow solid. The physical property of the compound 3-6 is shown in Table 21.

TABLE 21

Compound 3-6

[α]D$^{27}$+38.4° (c=1.85, CHCl$_3$); IR(neat film)1743, 1699,
1636, 1424, 1367, 1309, 1233, 1173, 1113, 1065, 861, 808cm$^{-1}$;
$^1$H NMR(400MHz, CDCl$_3$) δ 7.26-7.70(m, 5H), 6.60-6.75(br, 1H),
6.30-6.50(br, 1H), 5.65-6.20(br, 3H), 4.20-5.30(br, 8H),
3.80(s, 3H), 3.09(s, 3H), 2.90-3.30(br, 2H), 2.24(s, 3H),
2.15(s, 3H), 1.68(s, 3H), 1.46(s, 9H); $^{13}$C NMR(100MHz, CDCl$_3$) δ
170.4, 149.7, 148.8, 147.0, 142.9, 142.6, 137.6, 132.3, 128.5, 127.8,
125.7, 115.2, 115.2, 114.0, 113.2, 113.1, 113.0, 113.0, 112.9, 101.8,
96.3, 95.4, 81.1, 74.1, 73.3, 60.3, 60.2, 59.9, 54.0, 54.0, 52.6, 50.5,
37.5, 31.9, 28.3, 20.1, 15.7, 9.9

Example 4

Processes and all products in each process in synthesis of the compound 4-8 contained in general formula 2 are shown in following synthesis process D.

Synthetic Process D:
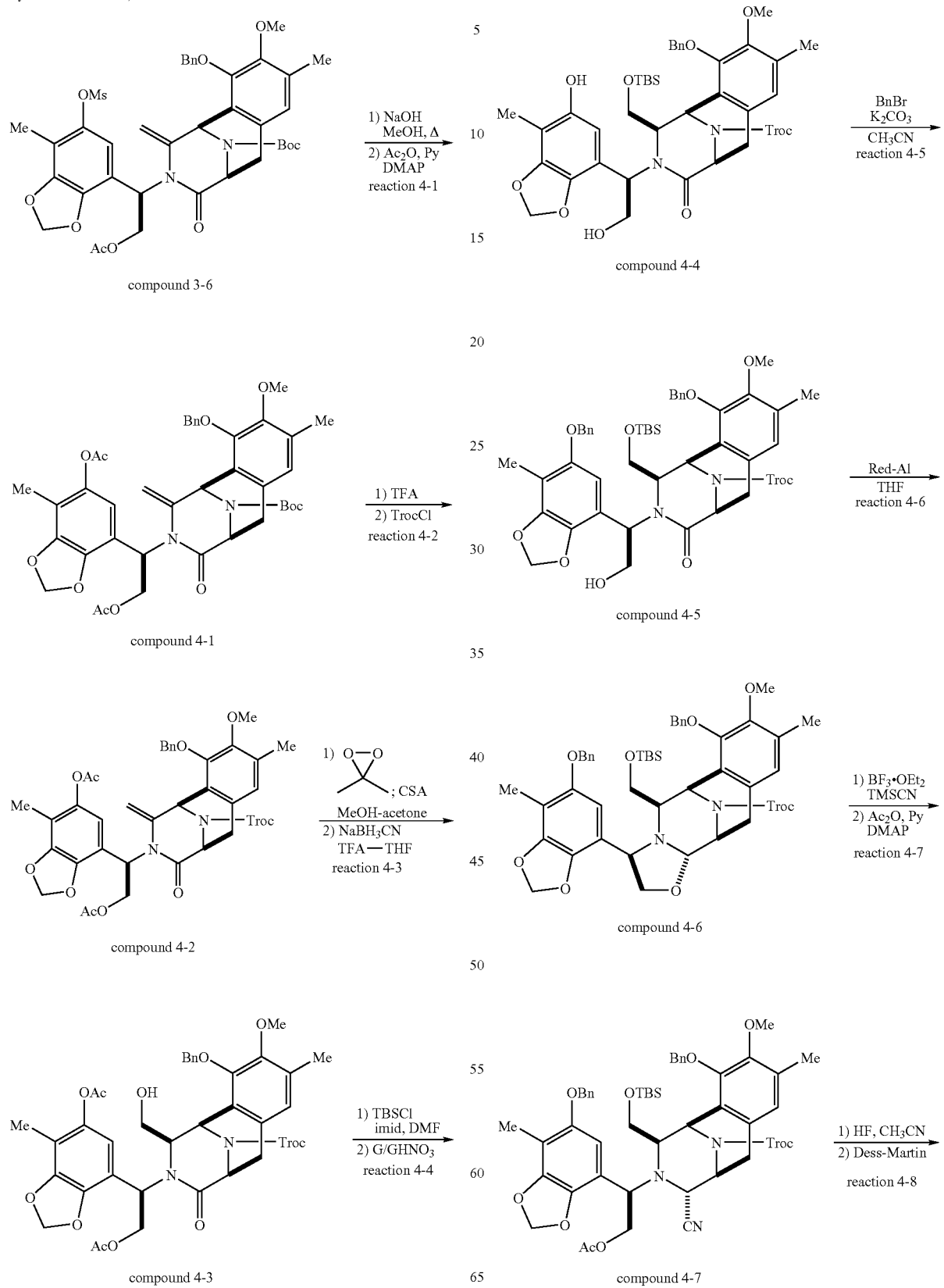

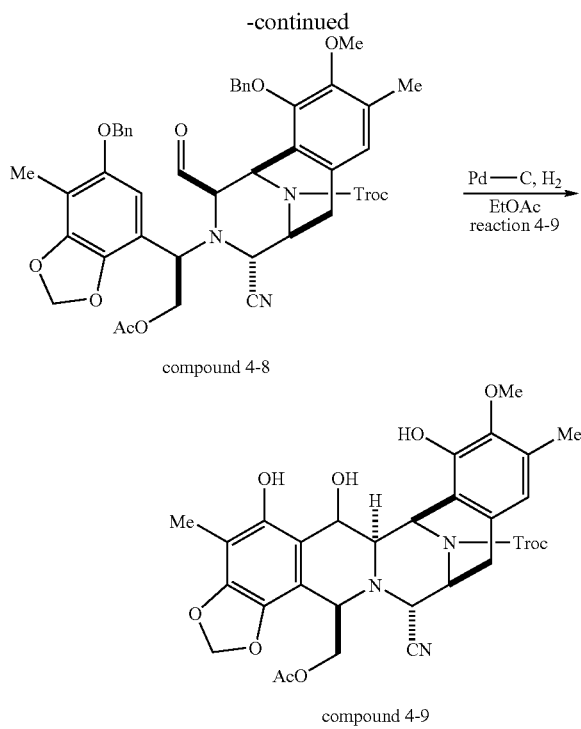

compound 4-8 compound 4-9

Detail of Synthesis of D;

Synthesis of Compound 4-1

2N NaOH aqueous solution (0.5 ml, 1 mmol) was added to MeOH solution (1.5 ml) of the compound 3-6 (120 mg, 0.157 mmol) was added and refluxed by heating for 2.5 hours. $Et_2O$ and water were added to the reaction solution and acidificated by 1N HCl aqueous solution, then extracted by EtOAc. The organic layer was washed by saturated $NaHCO_3$ aqueous solution and brine and concentrated by vacuum. To the residue, pyridine (0.26 ml, 3.2 mmol) acetic acid anhydride (0.15 ml, 1.6 mmol) and DMPA (1 mg, 0.008 mmol) were added at room temperature. After concentrated by vacuum, the residue was purified by silica gel chromatography (in 30% EtOAc n-hexane). Thus the compound 4-1 (106 mg, 0.145 mmol, 93%) was obtained as a white solid. The physical property of the compound 4-1 is shown in Table 22.

TABLE 22

Compound 4-1

$[\alpha]D^{26}$+46.6° (c=1.27, $CHCl_3$); IR(neat film)1766, 1746, 1699, 1634, 1484, 1427, 1368, 1307, 1208, 1183, 1109, 1081, 937, 913, 862; $^1$H NMR(40MHz, $CDCl_3$) δ 7.26-7.42(m, 5H), 6.64(br, 1H), 6.13(br, 1H), 5.70-5.95(br, 3H), 4.15-5.30(br, 8H), 3.73 (s, 3H), 2.90-3.20(br, 2H), 2.19(s, 3H), 2.17(s, 3H), 1.89(s, 3H), 1.51(s, 3H), 1.39(s, 9H); $^{13}$C NMR(100MHz, $CDCl_3$) δ 170.4, 169.2, 169.1, 149.8, 149.7, 149.7, 148.8, 146.8, 146.7, 144.3, 141.8, 140.4, 137.6, 137.6, 132.1, 132.1, 128.6, 128.5, 128.0, 128.0, 128.0, 127.9, 127.8, 127.7, 127.7, 127.7, 127.6, 127.5, 127.5, 127.5, 127.5, 125.7, 125.7, 125.7, 125.7, 115.3, 115.2, 115.2, 115.2, 115.2, 112.6, 112.2, 112.2, 112.2, 112.2, 101.6, 101.5, 81.0, 81.0, 81.0, 74.1, 74.1, 74.1, 73.6, 60.2, 59.6, 54.0, 52.8, 52.7, 52.7, 52.5, 52.5, 50.8, 50.8, 50.7, 50.7, 50.7, 32.0, 28.3, 20.6, 20.6, 20.0, 15.7, 9.3;

Synthesis of Compound 4-2

To the $CH_2Cl_2$ (12 ml) solution of the compound 4-1 (2.56 g, 3.51 mmol), TFA (3.0 ml, 39 mmol) was added at room temperature and stirred for 4 hours. The reaction solution was poured into saturated $NaHCO_3$ aqueous solution and extracted by $CH_2Cl_2$. After organic layer was concentrated by vacuum, the residue is dissolved in $CH_2Cl_2$ (12 ml) and saturated $NaHCO_3$ aqueous solution (20 ml) was added. To the reaction solution, TrocCl (0.47 ml, 3.5 mmol) was added and stirred for 10 minutes. The organic layer is dried by $MgSO_4$ and concentrated by vacuum. The residue was purified by silica gel chromatography (in 40% EtOAc n-hexane). Thus the compound 4-2 (2.08 g, 2.59 mmol, 1.74%) is obtained as a white powder. The physical property of the compound 4-2 is shown in Table 23.

TABLE 23

Compound 4-2

$[\alpha]D^{26}$+39.5 39.5(c=1.07, $CHCl_3$); IR(neat film)1763, 1724, 1684, 1636, 1486, 1429, 1368, 1353, 1298, 1222, 1209, 1184, 1124, 1078, 1031, 913, 863; $^1$H NMR(400MHz, $CDCl_3$) δ 7.31-7.50(m 5H), 6.72 & 6.74(s, 1H), 6.22 & 6.20(s, 1H), 6.00 & 5.96(s, 1H), 5.87 & 5.77 (s, 2H), 4.50-5.25(m, 9H), 4.37 & 4.29(s, 1H), 3.79(s, 3H), 3.10-3.30(m 2H), 2.25(s, 3H), 2.24(s, 3H), 1.95(s, 3H), 1.55 (s, 3H); $^{13}$C NMR(100MHz, $CDCl_3$) δ 170.3, 169.2, 149.8, 144.3, 141.8, 137.4, 132.5, 128.5, 128.5, 127.9, 127.8, 127.6, 125.7, 124.8, 115.0, 112.5, 112.2, 101.5, 95.1, 75.0, 74.0, 73.8, 60.2, 53.9, 53.3, 52.5, 32.2, 31.8, 20.6, 19.9, 15.7, 9.2;

Synthesis of Compound 4-3

To the MeOH (15.0 ml) solution of the compound 4-2 (681 mg, 0.847 mmol) dimethyloxilan (0.1M acetone solution, 15 ml, 1.5 mmol) was added at 0° C. and stirred for 2 hours. To the reaction solution, $Na_2SO_4$ (10 g) was added and stirred for 10 minutes, then CSA (7.2 mg, 0.03 mmol) was added and the temperature is elevated to room temperature. To the reaction solution, pyridine (25 µl, 0.31 mmol) was added so as to neutralize, then filtrated and concentrated by vacuum. The residue was purified by silica gel chromatography (in 50% EtOAc n-hexane) and the methoxy compound was obtained as a yellow powder.

THF solution (0.80 ml) of methoxy compound was added into TFA solution (4.0 ml) of $NaBH_3CN$ (160 mg, 2.54 mmol) at 0° C. and stirred for 40 minutes. $CHCl_3$ was added to the reaction solution and neutralized by saturated $NaHCO_3$ aqueous solution. The residue was passed through a column of basic alumina by EtOAc, then concentrated by vacuum. The residue was purified by silica gel chromatography (in 50% EtOAc n-hexane). Thus the compound 4-3 (150 mg, 0.182 mmol, 7.4%) was obtained as a white powder. The physical property of the compound 4-3 is shown in Table 24.

TABLE 24

Compound 4-3

$[\alpha]D^{22}$+33.2(c=1.23, $CHCl_3$); IR(neat film)3510, 1764, 1722, 1664, 1484, 1428, 1369, 1342, 1304, 1227, 1185, 1126, 1062, 938, 911cm$^{-1}$; IR NMR(400MHz, CDCl3) δ 7.54(d, J=6.8Hz, 2H), 7.38-7.48(m, 3H), 6.83 & 6.80(s, 1H), 6.36 & 6.33(s, 1H), 5.78-5.87(m, 3H), 5.40(br, 1H), 5.26-5.30(m, 1H), 5.11-5.16 (m 1H), 4.70-4.93(m, 3H), 4.52(br, 1H), 4.44(m, 1H), 3.91 & 3.87 (s, 3H), 3.55-3.65(br, 2H), 3.00-3.30(m, 3H), 2.29 & 2.28(s, 3H), 2.22(s, 3H), 1.95(s, 3H); $^{13}$C NMR(100MHz, $CDCl_3$) δ 170.4, 170.3, 170.2, 169.8, 169.1, 152.0, 151.6, 149.4, 149.0, 148.5, 146.5, 146.4, 144.3, 144.2, 142.0, 142.0, 135.2, 135.2, 133.4, 133.2, 129.4, 129.2, 129.2, 129.1, 129.0, 129.0, 128.9, 127.3, 127.2, 122.3, 121.8, 113.7, 113.5, 113.1, 113.0, 101.7, 101.6, 95.2, 95.1, 77.2, 76.4, 75.2, 75.1, 62.7, 62.6, 6.5, 6.5, 59.5, 53.9, 53.2, 47.5, 46.9, 31.9, 31.6, 2.7, 2.6, 2.6, 15.7, 9.3;

Synthesis of Compound 4-4

To the DMF solution (0.10 ml) of the compound 4-3 (101 mg, 0.123 mmol) and imidazole (21.3 mg, 0.313 mmol), TBSCl (28.0 mg, 0.186 mmol) was added at room temperature and stirred for 2 hours. The reaction solution was purified by silica gel chromatography (in 40% EtOAc n-hexane) and silanylether (106 mg, 0.127 mmol, 92%) was obtained as an oil. Silanylether (524 mg, 0.560 mmol) was dissolved in G/GHNO$_3$ solution (8.0 ml) and stirred for 2.5 hours at 40° C. EtOAc is added to the reaction solution and washed by 1N HCl aqueous solution, saturated NaHCO$_3$ aqueous solution and brine. The organic layer was dried by Na$_2$SO$_4$ and concentrated by vacuum. The residue is purified by silica gel chromatography (in 50% EtOAc n-hexane). Thus the compound 4-4 (405 mg, 0.475 mmol, 85%) is obtained as a yellow powder. The physical property of the compound 4-4 is shown in Table 25.

TABLE 25

Compound 4-4

$[\alpha]D^{23}$-33.7° (c=1.48, CHCl$_3$); IR(neat film)3309,
1723, 1640, 1423, 1345, 1304, 1257, 1133, 1127, 1095, 838cm$^{-1}$;
$^1$H NMR(400MHz, CDCl$_3$) δ 7.35-7.54(m 5H), 6.87 & 6.83(s, 1H),
6.30(br, 1H), 5.35-5.73(m 5H), 5.17-5.28(m, 1H),
5.06-5.16(m, 1H), 4.98 & 4.90(d, J=12.0Hz, 1H),
4.60-4.86(m, 3H), 4.27-4.40(m, 3H), 4.08(br, 1H),
3.80 & 3.74(s, 3H), 3.15-3.35(m, 3H), 2.28(s, 3H), 1.94 & 1.91
(s, 3H), 0.69 & 0.68(s, 9H), -0.27 & -0.30(s, 3H), -0.32 & -0.35
(s, 3H); $^{13}$C NMR(100MHz, CDCl$_3$) δ 151.9, 151.3, 150.1, 149.4, 148.7,
146.0, 136.6, 136.4, 133.2, 132.8, 129.2, 129.1, 128.7, 128.7, 128.6,
128.5, 128.4, 128.4, 126.5, 126.3, 123.2, 116.1, 106.3, 106.2, 105.0,
100.2, 95.0, 75.5, 75.3, 75.1, 68.3, 67.3, 63.1, 62.9, 62.0, 60.2,
58.7, 58.7, 53.6, 53.0, 48.8, 47.9, 32.2, 25.5, 17.8, 17.8, 15.6,
15.6, 8.4, 8.4, -5.9, -6.0, -6.1, -6.2

Synthesis of Compound 4-5

To the CH$_3$CN (6.0 ml) solution of the compound 4-4 (404 mg, 0.474 mmol) and K$_2$CO$_3$ (196 mg, 1.42 mmol) BnBr (73.0 μl, 0.615 mmol) was added and refluxed by heat for 1 hour. CHCl$_3$ was added to the reaction solution and filtrated by Celite, then concentrated by vacuum. The residue was purified by silica gel chromatography (in 50% EtOAc n-hexane). Thus the compound 4-5 (409 mg, 0.434 mmol, 91%) was obtained as a yellow powder. The physical property of the compound 4-5 is shown in Table 26.

TABLE 26

Compound 4-5

$[\alpha]D^{23}$-37.4° (c=2.11, CHCl$_3$); IR(neat film)3749,
1717, 1419, 1340, 1253, 1111, 838cm$^{-1}$; $^1$H NMR(400MHz, CDCl$_3$) δ
7.30-7.60(m, 10H), 6.77 & 6.73(s, 1H), 5.83(s, 1H), 5.77(br, 2H),
5.69(s, 1H), 5.51(br, 1H), 5.22 & 5.21(d, J=10.0Hz, 1H), 5.14
(br, 1H), 5.00 & 4.88(d, J=11.6Hz, 1H), 4.74(d, J=11.6Hz, 1H),
4.68(d, J=10.0Hz, 1H), 4.59(d, J=10.8Hz, 1H), 4.50 & 4.46
(d, J=11.6Hz, 1H), 4.37 & 4.25, (br, 1H), 4.30 & 4.29(d,
J=10.8Hz, 1H), 4.05 & 3.95(br, 2H), 3.80 & 3.75(s, 3H),
3.13-3.37(m, 3H), 1.99 & 1.96(s, 9H), -0.27 & -0.32(s, 3H), -0.33
& -0.36(s, 3H); $^{13}$C NMR(100MHz, CDCl$_3$) δ 170.2, 152.1,
152.1, 150.0, 148.8, 146.2, 137.2, 137.1, 136.5, 133.1, 129.2,
128.7, 128.6, 128.6, 128.5, 128.3, 128.0, 127.9, 127.8, 126.4, 126.3,
123.3, 115.8, 108.1, 102.6, 100.6, 75.5, 75.3, 75.2, 70.8, 67.5, 66.7,
63.5, 62.3, 60.3, 60.3, 59.8, 53.4, 52.7, 47.9, 47.2, 32.0, 31.5, 25.5,
22.6, 17.8, 15.5, 14.1, 8.7, -6.0, -6.3

Synthesis of Compound 4-6

To the THF solution (2.0 ml) of the compound 4-5 (224 mg, 0.238 mmol), Red-Al (1.3M toluene solution, 0.25 ml, 0.325 mmol) was added at 0° C. 1N HCl aqueous solution was added to the reaction solution and extracted by ETOAc. The organic layer was washed by saturated NaHCO$_3$ aqueous solution and brine, dried by MgSO$_4$ and concentrated by vacuum. The residue was purified by silica gel chromatography (in 30% EtOAc n-hexane). Thus the compound 4-6 (181 mg, 0.195 mmol, 82%) was obtained as a white solid. The physical property of the compound 4-6 is shown in Table 26.

TABLE 27

Compound 4-6

$[\alpha]D^{22}$-37.4° (c=1.19, CHCl$_3$); IR(neat film)1717,
1435, 1263, 1118, 1024, 840 cm$^{-1}$; $^1$H NMR(400MHz, CDCl$_3$) δ 7.58
(d, J=8.0Hz, 1H), 7.50(d, J=6.8Hz, 1H), 7.26-7.49 (m, 8H),
6.77 & 6.73(s, 1H), 6.41 & 6.40(s, 1H)5.86(s, 1H), 5.77(s, 1H),
5.57 & 5.51(s, 1H), 5.41(br, 1H), 5.21(dd, J=10.4, 10.4Hz, 1H),
4.93(dd, J=7.2, 6.0Hz, 1H), 4.69-5.02(m, 5H), 4.20-4.35(m,
3H), 3.87 & 3.83(s, 3H), 3.74(m, 1H), 3.14-3.35(m, 3H), 2.73
(dd, J=17.6, 6.0Hz, 1zh9), 2.21(s, 3H), 2.09(s, 3H), 0.71 & 0.69
(s, 9H), -0.21 & -0.26(s, 3H), -0.27 & 0.31(s, 3H); $^{13}$C NMR
(100MHz, CDCl$_3$) δ 153.1, 153.5, 151.8, 149.5, 149.4, 148.1, 147.6,
146.5, 138.2, 137.4, 137.3, 131.4, 131.2, 130.2, 129.9, 128.6, 128.5,
128.4, 128.3, 128.0, 127.9, 127.7, 127.2, 127.2, 125.5, 125.0, 124.4,
120.7, 120.6, 107.9, 101.9, 101.7, 100.7, 100.6, 95.4, 92.1, 92.1,
75.5, 75.2, 75.0, 74.8, 70.3, 68.9, 68.3, 68.1, 66.7, 60.5, 60.3,
60.2, 60.1, 60.0, 59.9, 48.5, 48.1, 47.5, 46.7, 30.7, 30.5, 25.6,
17.8, 15.7, 15.7, 8.7, -5.9, -5.9, -6.0, -6.0

Synthesis of Compound 4-7

To the CH$_2$Cl$_2$ (5.0 ml) solution of the compound 4-6 (2.95 g, 0.318 mmol) and TMSCN (127 μl, 0.952 mmol, 3.0 equivalent), BF$_3$-OEt$_2$ (in 1.0M CH$_2$Cl$_2$ solution, 480 μl, 0.48 mmol) was added at 0° C. The reaction solution was poured into saturated NaHCO$_3$ aqueous solution, extracted by CH$_2$Cl$_2$, and organic layer was dried by MgSO$_4$ then concentrated by vacuum. The residue was purified by silica gel chromatography (in 50% EtOAc n-hexane) and nitrile compound (221 mg, 0.232 mmol) was obtained as a white solid. To the reaction solution of nitrile compound (221 mg, 0.232 mmol), acetic anhydride (1.0 ml) and pyridine (2.0 ml), DMPA (5.6 mg, 0.05 mmol) was added and stirred for 1 hour at room temperature. After reaction solution is concentrated by vacuum, residue is purified by silica gel chromatography (in 30% EtOAc n-hexane) and the compound 4-7 (213 mg, 0.214 mmol, 92%) was obtained as a white solid. Physical properties of the Compound 4-7 are shown in Table 28.

TABLE 28

Compound 4-7

$[\alpha]D^{23}$+49.9° (c=1.82, CHCl$_3$); IR(neat film)1720,
1430, 1251, 1122, 840cm$^{-1}$; $^1$H NMR(400MHz, CDCl$_3$) δ 7.26-7.65
(m, 10H), 6.52, 6.49(s, 1H), 6.10(br, 1H), 5.67(s, 1H), 5.50 & 5.35
(s, 1H), 5.37(s, 1H), 4.55-5.30(m, 8H), 5.50-5.55(m, 3H), 3.89 &
3.83 (s, 3H), 3.65-3.80 8br, 1H), 3.40-3.55(br, 2H), 2.85 & 2.80
(dd, J=17.6, 8.0Hz, 1H), 2.20-2.30(br, 6H), 1.90-2.00(br, 3H),
1.53 & 1.65(d, J=17.0Hz, 1H), 0.77(br, 9H), -0.04 & 0.11
(s, 3H), -0.08 & -0.14(s, 3H); $^{13}$C NMR(100MHz, CDCl$_3$) δ 170.2,
170.1, 152.6, 152.2, 151.0, 150.8, 149.0, 148.9, 147.6, 147.0, 146.7,
139.7, 139.7, 137.6, 137.4, 137.2, 131.2, 130.9, 130.6, 128.6, 128.6,
128.5, 128.4, 128.1, 128.0, 127.8, 127.7, 127.1, 125.4, 124.9, 124.9,
124.8, 117.9, 1117.9, 117.8, 115.6, 115.6, 109.4, 109.3, 103.6, 103.5,
100.5, 95.2, 95.1, 75.6, 75.1, 74.8, 70.4, 70.2, 63.3, 63.1, 61.9,
61.2, 60.2, 59.3, 54.2, 54.0, 51.8, 51.6, 50.2, 49.3, 49.1, 48.7,
29.8, 29.7, 25.7, 20.8, 20.8, 18.1, 18.1, 15.5, 8.9, -5.7, -5.8,
-6.0, -6.1;

Synthesis of Compound 4-8

To the CH$_3$CN (2.0 ml) solution of the compound 4-7 (200 mg, 0.20 mmol), HF (48 wt % aqueous solution, 1.0 ml, 28 mmol) was added and stirred for 3 hours. The reaction solution is poured into saturated NaHCO$_3$ aqueous solution and extracted by EtOAc. The organic layer was washed by brine and concentrated by vacuum. The residue was purified by silica gel chromatography (in 40% AcOEt n-hexane) and alcohol compound (180 mg, 0.20 mmol, 100%) was obtained as a white solid. To the CH$_2$Cl$_2$ (2.5 ml) solution of Dess-Martin reagent (103 mg, 0.243 mmol) was added at room temperature and stirred for 30 minutes. Reaction was stopped by adding 2-propanol (20 μL), then Et$_2$O was added, filtrated by Celite and concentrated by vacuum. The residue was dissolved in EtOAc and washed by saturated NaHCO$_3$ aqueous solution and brine. The organic layer was dried by MgSO$_4$ and concentrated by vacuum. The residue was purified by silica gel chromatography (in 40% EtOAc n-hexane) and the compound 4-8 (165 mg, 0.188 mmol, 92%) was obtained as a white solid. Dess-Martin reagent is shown by following chemical formula.

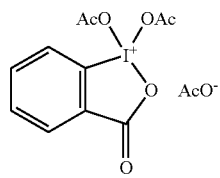

Physical properties of the Compound 4-7 are shown in Table 29.

TABLE 29

Compound 4-8

[α]$_D^{24}$+23.2° (c=0.90, CHCl$_3$); IR(neat film)1732, 1607, 1584, 1488, 1382, 1315, 1238, 1122, 1035, 939, 906, 826cm$^{-1}$; $^1$H NMR(400MHz, CDCl$_3$) δ 9.17 & 9.12(d, 2.8H), 7.23-7.45(m, 10H), 6.61 & 6.59(s, 1H), 5.93(br, 1H), 5.80(br, 1H), 5.75 & 5.72(br, 1H), 5.62(br, 1H), 5.21 & 5.18(d, J=10.8Hz, 1H), 4.65-5.00(m, 8H), 4.27-4.52(M, 3H), 3.78 & 3.71(s, 3H), 3.68(br, 1H), 3.13 & 3.08 (dd, J=17.6, 8.0Hz, 1H), 2.12(br, 1H), 2.04-2.11(br, 6H), 2.01 & 2.01(s, 3H); $^{13}$C NMR(100MHz, CDCl$_3$) δ 196.9, 196.4, 170.2, 152.4, 152.1, 146.7, 139.8, 137.1, 137.1, 132.0, 130.5, 128.6, 128.5, 128.4, 128.0, 127.9, 127.9, 127.8, 127.2, 127.2, 127.0, 125.0, 124.9, 123.9, 113.5, 113.4, 110.4, 103.9, 100.9, 95.0, 75.3, 74.4, 70.5, 70.4, 68.9, 68.4, 62.3, 60.5, 56.8, 51.8, 51.7, 50.1, 49.1, 47.2, 30.0, 20.9, 15.8, 9.0

Synthesis of Compound 4-8

THF (1.2 ml) solution of the compound 4-8 (51.2 mg, 0.058 mmol) and 10% Pd—C (51.1 mg, 0.024 mmol) was stirred for 18 hours at room temperature under the 1 atmospheric pressure of hydrogen gas. The reaction solution was filtrated by Cellite and concentrated by vacuum. The residue was purified by silica gel chromatography (in 50% EtOAc n-hexane) and the compound 4-9 (34.2 mg, 0.049 mmol, 84%) was obtained as a yellow film. Physical properties of the Compound 4-7 are shown in Table 30.

TABLE 30

Compound 4-9

[α]$_D^{24}$+23.1° (c=1.37, CHCl$_3$); IR(neat film)3749, 1722, 1623, 1587, 1501, 1435, 1380, 1317, 1265, 1232, 1127, 1105, 1056, 1032, 1012, 965cm$^{-1}$; $^1$H NMR(400MHz, CDCl$_3$) δ 6.55(s, 1H), 5.92(s, 1H), 5.85 & 5.80(s, 1H), 5.83 8s, 1H), 4.91 & 4.87(d, J=8.0Hz, 1H), 4.87 & 4.85 8d, J=11.6Hz, 1H), 4.69 & 4.67(d, J=11.6Hz, 1H), 4.48 (d, 10.4Hz, 1H), 4.46(m, 1H), 4.19(br, 1H), 4.07(br, 1H), 3.77 & 3.76(s, 3H), 3.66(dd, J=10.8, 8.0Hz, 1H), 3.34 & 3.31 (dd, J=10.4, 2.8Hz, 1H), 3.25(dd, J=17.6, 8.0Hz, 1H), 2.85 & 2.80(d, J=17.6Hz, 1H), 2.25 & 2.24(s, 3H); $^{13}$C NMR TABLE 30-continued Compound 4-9

(100MHz, CDCl$_3$) δ 170.3, 153.1, 152.5, 149.3, 149.2, 145.9, 145.9, 144.0, 143.7, 142.5, 142.3, 135.4, 135.3, 131.6, 131.3, 130.1, 130.1, 123.1, 122.9, 117.0, 116.9, 115.9, 115.8, 110.0, 109.9, 108.0, 101.0, 95.3, 95.0, 75.3, 75.1, 68.9, 68.8, 64.1, 61.6, 61.5, 61.1, 61.0, 58.9, 58.8, 56.3, 49.6, 48.9, 47.1, 46.4, 30.5, 29.6, 20.2, 15.7, 15.7, 8.6

Example 5

Synthesis of compounds contained in general formula 1. Each process from reaction 5-1 to reaction 5-3 and products from each process are shown in synthetic process E.

Synthetic Process E;

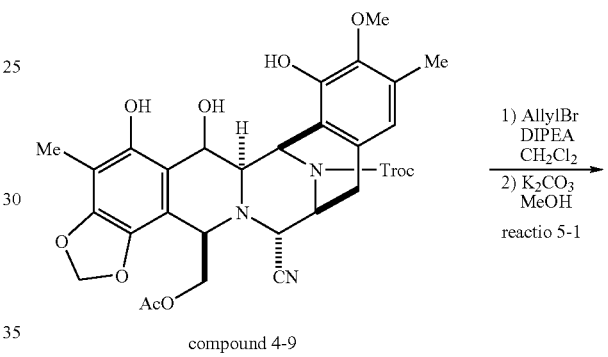

compound 4-9

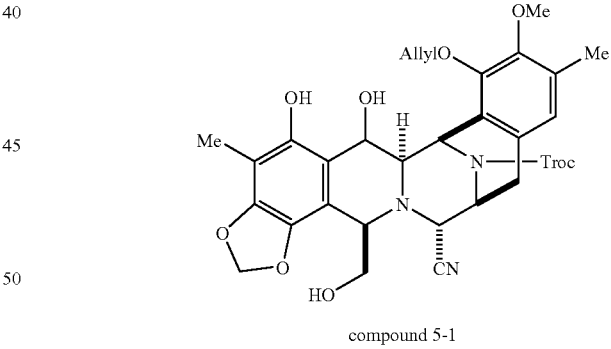

compound 5-1

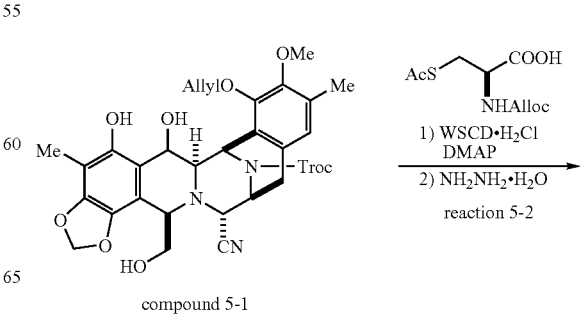

compound 5-1

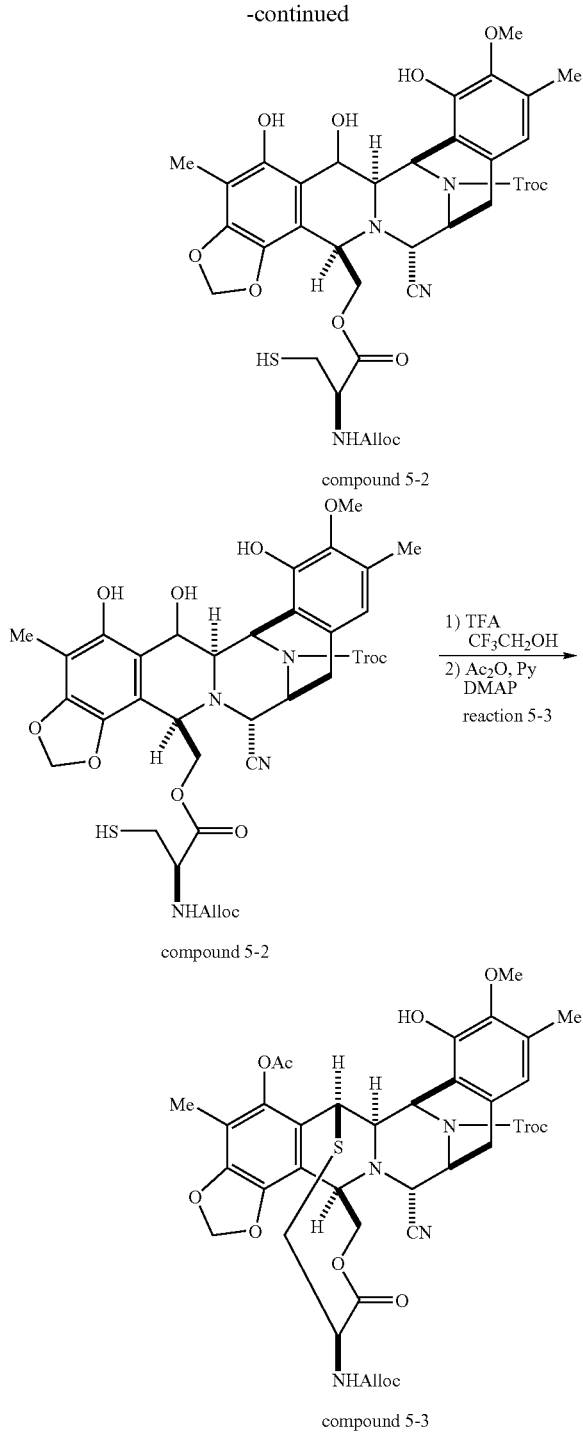

compound 5-2 compound 5-2 compound 5-3

Details of Synthetic Process E;

Synthesis of Compound 5-1

To the CH$_2$Cl$_2$ (1.2 ml) solution of the compound 4-9 (34.2 mg, 0.049 mmol) and i-Pr$_2$NEt (0.20 ml, 1.2 mmol), AllylBr (40 μl, 0.47 mmol) was added and heat refluxed for 3 hours. CH$_2$Cl$_2$ was added to the reaction solution, washed by 1N HCl aqueous solution, saturated NaHCO$_3$ aqueous solution and brine. The organic layer was dried by MgSO$_4$ and concentrated by vacuum. The residue was purified by silica gel chromatography (in 50% EtOAc n-hexane) and allylether (32.3 mg, 0.044 mmol, 89%) was obtained. To the MeOH (0.6 ml) solution of the allylether (32.3 mg, 0.044 mmol), K$_2$CO$_3$ (70.8 mg, 0.51 mmol) was added and stirred for 30 minutes at room temperature. EtOAc was added to the reaction solution, and washed by 10% citric acid, saturated NaHCO$_3$ aqueous solution and brine. The organic layer was washed by MgSO$_4$ and concentrated by vacuum. The residue was purified by silica gel chromatography (in 50% EtOAc n-hexane) and the compound 5-1 (30.3 mg, 0.044 mmol, 99%) was obtained as a colorless film. Physical properties of the Compound 5-1 are shown in Table 31.

TABLE 31

| Compound 5-1 |
|---|
| [α]$_D^{26}$+43.8° (c=1.11, CHCl$_3$); IR(neat film)3298, 1720, 1486, 1434, 1378, 1336, 1315, 1267, 1229, 1125, 1058, 1032, 965, 827cm$^{-1}$; $^1$H NMR(400MHz, CDCl$_3$) δ 9.59 & 9.57(s, 1H), 6.81 & 6.78(s, 1H), 6.20(m, 1H), 5.65-5.95(m, 4H), 5.40-5.60 (m, 2H), 4.60-5.00(m, 4H), 4.50(m, 2H), 4.20-4.40(m, 2H), 4.00 (m, 1H), 3.84 & 3.82(s, 3H), 3.60(m, 1H), 3.20-3.35(m, 3H), 2.86 (d, J=17.6Hz, 1H), 2.24 & 2.23(s, 3H), 2.06 & 2.04(s, 3H); $^{13}$C NMR (100MHz, CDCl$_3$) δ 152.8, 152.2, 149.4, 149.3, 148.7, 147.4, 147.0, 145.8, 135.4, 135.3, 133.0, 132.7, 132.0, 130.5, 130.1, 126.5, 126.5, 123.8, 123.0, 121.7, 121.3, 115.7, 115.7, 110.2, 109.5, 109.4, 107.9, 100.9, 100.9, 95.1, 15.0, 77.2, 76.1, 75.6, 75.5, 75.2, 68.9, 68.7, 68.5, 65.5, 65.5, 62.0, 61.4, 60.6, 60.6, 59.3, 59.3, 58.3, 58.2, 49.8, 48.6, 47.4, 47.0, 30.7, 30.7, 30.6, 15.8; |

Synthesis of Compound 5-2

To the CH$_2$Cl$_2$ (1.60 ml) solution of the compound 5-1 (51.0 mg, 0.073 mmol) and S-acetyl-N-alloccystein (42.7 mg, 0.173 mmol), WSCD.HCl (37.2 mg, 0.194 mmol) and DMAP (1.9 mg, 0.008 mmol) were added at room temperature. After stirred for 10 minutes, CH$_2$Cl$_2$ was added to the reaction solution, and washed by 1N HCl aqueous solution, saturated NaHCO$_3$ aqueous solution and brine. The organic layer was concentrated by vacuum, and the residue was purified by sihca gel chromatography (in 50% EtOAc n-hexane) and ester (64.0 mg, 0.070 mmol, 94%) was obtained as a yellow film.

To the CH$_3$CN (0.80 ml) solution of ester (29.5 mg, 0.032 mmol), hydrazine solution (upper layer of 1:3 mixture (by volume) of hydrazine hydride and CH$_3$CN$_3$, 35 μl) was added and stirred for 1.5 minutes at room temperature. CHCl$_3$ was added to the reaction solution, washed by 1N HCl aqueous solution, saturated NaHCO$_3$ aqueous solution and brine and dried by Na$_2$SO$_4$. Solution was evaporated off and the compound 5-2 (27.8 mg, 0.031 mmol, 98%) was obtained as a colorless film. Physical properties of the Compound 5-2 are shown in Table 32.

TABLE 32

| Compound 5-2 |
|---|
| [α]$_D^{24}$+22.8° (c=1.11, CHCl$_3$); IR(neat film)3297, 1718, 1507, 1436, 1375, 1338, 1298, 1263, 1125, 1102, 1059, 1032, 1013, 968, 939, 827cm$^{-1}$; $^1$H NMR(400MHz, CDCl$_3$) δ 9.50-9.65 (m, 1H), 7.26-7.40(m, 5H), 6.72-6.83(m, 1H), 6.23(m, 1H), 6.12 & 6.09(d, J=4.0Hz, 1H), 5.95(s, 1H), 5.88(m, 1H), 5.81, (s, 1H), 5.79 & 5.69(s, 1H) 5.20-5.60(m, 4H), 4.77-5.02(m, 3H), 4.63-4.72(m, 1H), 4.27-4.64(m, 4H), 4.08-4.27(m, 3H), 3.95-4.68 (m, 1H), 3.87(s, 3H), 3.89(s, 3H), 3.15-3.35(m, 2H), 2.70-3.05 (m, 1H), 2.88 8d, J=17.6Hz, 1H), 2.50-2.70(m, 2H), 2.27 & 2.25 (s, 3H), 2.08(s, 3H), 0.85-1.45(m, 2H); $^{13}$C NMR(100MHz, CDCl$_3$) δ 169.8, 169.5, 155.3, 152.8, 152.2, 149.6, 149.5, 148.6, 148.5, 147.5, 147.0, 145.9, 135.3, 132.7, 132.5, 132.4, 132.3, 132.0, 132.0, 131.0, 130.6, 126.7, 126.6, 123.9, 123.2, 121.7, 121.6, 121.1, 118.4, 118.2, 118.1, 115.6, 115.6, 110.0, 109.0, 109.2, 108.4, 108.2, 101.0, 95.2, 95.1, 76.2, 75.6, 75.6, 75.3, 68.9, 68.7, 68.6, 66.2, 66.1, 66.0, 65.1, 61.9, 61.4, 60.8, 60.7, 59.1, 58.8, 56.7, 55.2, 55.1, 54.8, 52.8, |

TABLE 32-continued

Compound 5-2

49.7, 48.8, 47.1, 46.9, 46.8, 31.6, 30.5, 30.3, 30.1, 27.2, 26.8, 26.5,
22.6, 15.9, 15.8, 15.8, 14.2, 14.1, 8.6;

Synthesis of Compound 5-3

To the trifluoroetanol solution of the compound 5-2 (24.6 mg, 0.028 mmol), TFA (10% 2,2,2-trifluoroetanol, 0.15 ml, 0.19 mmol) was added at room temperature and stirred for 3 hours. Benzene was added to the reaction solution and concentrated by vacuum. The obtained residue was dissolved in acetate anhydride (0.1 ml) and pyridine (0.2 ml), then DMAP (1.5 mg, 0.012 mmol) was added and stirred for 30 minutes. The reaction solution was concentrated by vacuum and the residue was purified in PTLC (30% EtOAc n-hexane). The compound 5-3 (18.0 mg, 0.020 mmol, 71%) was obtained as a colorless film. Physical properties of the Compound 5-3 are shown in Table 33.

TABLE 33

Compound 5-3

$[\alpha]_D^{23}$-22.2° (c=1.06, CHCl$_3$); IR(neat film)3402, 1759, 1721, 1510, 1431, 1372, 1332, 1309, 1265, 1236, 1193, 1125, 1101, 1-87, 1060, 1029, 1007, 983, 916, 826cm$^{-1}$; $^1$H NMR(400MHz, CDCl$_3$) δ 6.79 & 6.78(s, 1H), 6.18(m, 1H), 6.10(s, 1H), 6.01 & 5.99 (s, 1H), 5.94(m, 1H), 5.45-5.68(m, 2H), 5.22-5.35(m, 3H), 4.97-5.15(m, 3H), 4.65-4.90(m, 3H), 4.42-4.63(m, 5H), 4.33(br, 1H), 4.15-4.27(m, 4H), 3.81 & 3.87(s, 3H), 3.43(s, 1H), 3.12-3.29(m, 2H), 2.30-2.38(m, 2H), 2.29 & 2.28(s, 3H), 2.26 & 2.25(s, 3H), 2.03(s, 3H); 13C NMR(100MHz, CDCl$_3$) δ 170.4, 168.6, 168.5, 155.3, 152.6, 152.2, 149.5, 148.8, 148.7, 146.0, 146.0, 141.0, 140.3, 140.3, 134.6, 134.5, 132.9, 132.7, 132.7, 132.6, 130.1, 129.6, 127.1, 126.5, 125.1, 125.0, 119.5, 119.4, 118.1, 116.2, 116.2, 116.2, 116.0, 115.9, 113.9, 112.7, 112.6, 102.1, 102.1, 95.2, 95.0, 75.3, 75.3, 73.4, 72.7, 65.9, 61.3, 61.3, 60.4, 60.4, 59.4, 59.4, 58.4, 58.2, 58.0, 57.7, 53.8, 49.0, 48.1, 47.9, 47.7, 41.2, 41.1, 32.9, 32.9, 28.1, 27.7, 20.5, 20.4, 15.8, 15.8, 9.6;

Reference Example 1

Processes and products at each process regarding the synthesis of ecteinascidin 743 from the compound 5-3 is shown in following synthetic process F.

Synthetic process F;

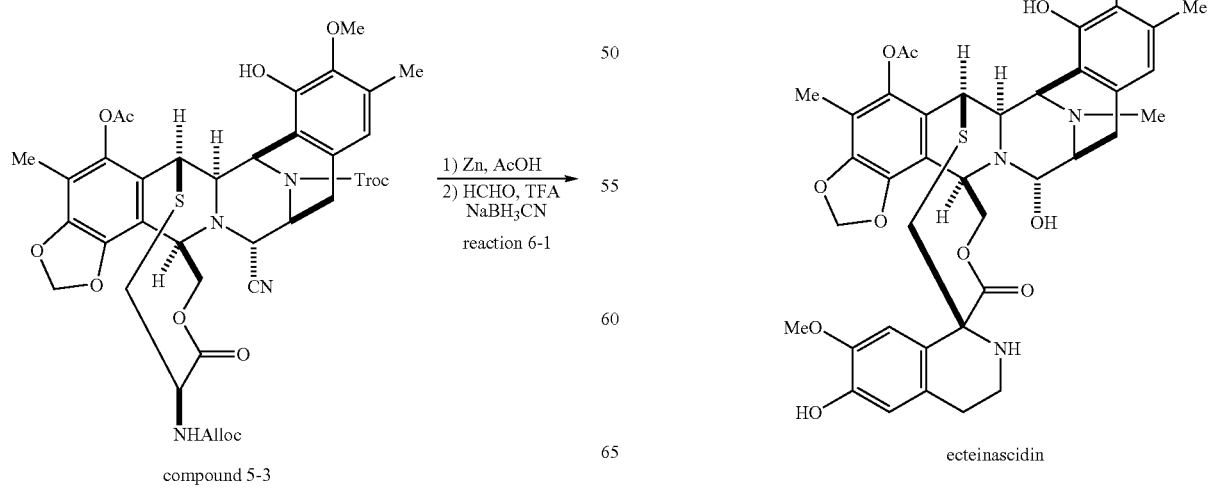

Detail of Synthesis of F;

Synthesis of Compound 6-1

To the Et$_2$O (0.40 ml) solution of the compound 5-3 (17.3 mg, 0.0190 mmol) and zinc powder (96.1 mg, 1.47 mmol), AcOH (0.20 ml) was added at room temperature and stirred for 2.5 hours. Reaction solution was filtrate by Celite and concentrated by vacuum. EtOH was added to the residue and washed by saturated NaHCO$_3$ and brine. The organic layer was concentrated by vacuum and the residue was purified refined by PTLC (in 50% EtOAc n-hexane), thus amine (12.8 mg, 0.0175 mmol, 92%) was obtained as a colorless film. To amine (5.6 mg, 0.0076 mmol), aqueous solution (30 µl) of formalin and MeOH (0.4 ml) solution of NaBH$_3$CN (12 mg, 0.19 mmol), AcOH (0.10 ml) was added and stirred at room temperature for 1 hour. After concentrated by vacuum, the reaction solution was diluted by EtOAc and washed by saturated NaHCO$_3$ and brine. The organic layer was concentrated by vacuum, and the residue was purified by PTLC (in 50% EtOAct n-hexane), then the compound 6-1 (5.5 mg, 0,0074 mmol, 96%) was obtained as a colorless film. Physical properties of the Compound 6-1 are shown in Table 34.

TABLE 34

Compound 6-1

[α]$D^{23}$−25.6° (c=0.86, CHCl$_3$); IR(neat film)3401, 1759, 1724, 1507, 1446, 1372, 1331, 1235, 1194, 1145, 1106, 1088, 1067, 998, 915cm$^{-1}$; $^1$H NMR(400MHz, CDCl$_3$) δ 6.78(s, 1H), 6.08(s, 1H), 6.08 (m, 1H), 5.99(s, 1H9, 5.96(m, 1H), 5.45(d, J=17.6Hz, 1H), 5.31(d, J=17.6Hz, 1H), 5.25(d, J=10.8Hz, 2H), 5.02 (d, J=12.0Hz, 1H), 4.80(m, 2H), 4.40-4.55(m, 3H), 4.27-4.40(m, 2H), 4.24(s, 1H), 4.19(m, 1H), 4.16(m, 2H), 3.79(s, 3H), 3.35-3.45 (m 2H), 2.85-2.97(m, 2H), 2.29(s, 3H), 2.27(s, 3H), 2.20-2.40 (m, 1H), 2.20(s, 3H), 2.13(d, J=16.4Hz, 1H), 2.03(s, 3H); $^{13}$C NMR(100 MHz, CDCl$_3$) δ 170.4, 168.6, 155.4, 150.8, 148.8, 145.7, 140.9, 140.3, 134.5, 132.8, 131.7, 129.9, 124.7, 124.6, 120.2, 118.0, 116.6, 113.5, 113.3, 102.0, 72.9, 65.8, 61.3, 60.4, 59.2, 59.1, 55.0, 54.5, 53.8, 41.6, 41.5, 32.8, 23.7, 20.4, 15.7, 9.6

Synthesis of Compound 6-2

To the CH$_2$Cl$_2$ (0.70 ml) solution of the compound 6-1 (8.6 mg, 0.012 mmol), Pd(PPh$_3$)Cl$_2$ (3.2 mg, 0.0045 mmol) and AcOH (15 µl, 0.26 mmol, 23 equivalent), n-Bu$_3$SnH (30 µl, 0.11 mmol) was added at room temperature for 20 minutes. The reaction solution was diluted by Et$_2$O, and after filtrated by Celite, concentrated by vacuum. The residue was refined by silica gel chromatography (in 10% MeOH CH$_2$Cl$_2$) and amine (6.4 mg, 0.010 mmol, 89%) was obtained as a white film. To the mixed solvent of DMF (0. 15 ml) and CH$_2$Cl$_2$ (0.15 ml) of amine (3.7 mg, 0.0059 mmol), 4-formyl-N-metylpyridine (16.5 mg, 0.057 mmol, 10 equivalent) was added and stirred at room temperature for 15 min. DBU (8.0 µl, 0.053 mmol) was added to the reaction solution and stirred at room temperature for 15 min. The reaction solution was diluted by CH$_2$Cl$_2$ (0.30 ml), then saturated citric acid aqueous solution (100 µl) was added and stirred for 40 minutes. Saturated NaHCO$_3$ aqueous solution and Et$_2$O were added, then Et$_2$O layer was concentrated by vacuum. The residue was purified by PTLC (in 70% EtOAc n-hexane), and the compound 6-2 (2.0 mg, 0.0032 mmol, 54%) was obtained as a white film. Physical properties of the Compound 6-2 are shown in Table 35.

TABLE 35

Compound 6-2

[α]$D^{22}$+153° (c=0.20, CHCl$_3$); IR(neat film)3447, 1763, 1723, 1622, 1589, 1500, 456, 373, 1270, 1236, 1194, 1160, 1145, 1108, 1087, 1063cm$^{-1}$; $^1$H NMR(400MHz, CDCl$_3$) δ 6.49(s, 1H), 6.11 (s, 1H), 6.03(s, 1H), 5.69(s, 1H), 5.09(d, J=11.6Hz, 1H), 4.66 (br, 1H), 4.39(s, 1H), 4.24(d, J=4.8Hz, 1H), 4.22(d, J=11.6Hz,, 1H), 4.16(d, J=2.8Hz, 1H), 3.76(s, 3H), 3.54 (d, J=4.8Hz, 1H), 3.43(dd, J=9.6, 2.8Hz, 1H), 2.90(dd, J=18.4, 9.6Hz, 1H), 2.84(d, J=13.6Hz, 1H), 2.70(d, J=18.4Hz, 1H), 2.57(d, J=13.6Hz, 1H), 2.33(s, 3H9, 2.24(s, 3H), 2.14(s, 3H), 2.04(s, 3H); $^{13}$C NMR(100MHz, CDCl$_3$) δ 186.7, 168.5, 160.5, 147.1, 146.4, 142.9, 141.6, 140.7, 130.4, 129.8 121.7, 121.7, 120.0, 117.9, 117.1, 113.5, 113.3, 102.2, 61.7, 61.4, 60.3, 59.8, 58.9, 54.6, 43.2, 41.6, 36.8, 24.1, 20.4, 15.8, 9.7

Synthesis of Compound 6-3

To the EtOH (0.25 ml) solution of the compound 6-2 (2.0 mg, 0.0026 mmol) and 3-hydroxy-4-methoxyphenylethylamine (12.4 mg, 0.062 mmol), NaOAc (7.4 mg, 0.090 mmol) was added at room temperature and stirred for 5.5 hours. After concentrated by vacuum, the residue was purified by PTLC (5% MeOH in CH$_2$Cl$_2$) and the compound 6-3 (2.4 mg, 0.0031 mmol, 96%) was obtained as a white film. Physical properties of the Compound 6-3 are shown in Table 36.

TABLE 36

Compound 6-3

[α]$D^{23}$−57.0° (c=0.24, CHCl$_3$); IR(neat film)3437, 2931, 1743, 1591, 1507, 1456, 1369, 1236, 1193, 1107, 1087, 1053, 1028cm$^{-1}$; $^1$H NMR(400MHz, CDCl$_3$) δ 6.60(s, 1H), 6.48(s, 1H), 6.45(s, 1H), 6.05(s, 1H), 5.98(s, 1H), 5.73(s, 1H), 5.38(br, 1H), 5.02(d, J=11.6Hz, 1H), 4.57(br, 1H), 4.33(s, 1H), 4.28(d, J=5.2Hz, 1H), 4.19(d, J=2.8Hz, 1H), 4.12(dd, J=11.6, 2.8Hz, 1H), 3.79(s, 3H), 3.63(s, 3H), 3.51(d, J=4.8Hz, 1H), 3.42(m, 1H), 3.10(ddd, J=11.6, 10.8, 4.0Hz, 1H), 2.94(m, 2H), 2.78(m, 1H), 2.62 (m, q1H), 2.47(m, 1H), 2.35(m, 1H), 2.32(s, 3H), 2.27(s, 3H), 2.20(s, 3H), 2.09(m, 1H), 2.04(s, 3H); $^{13}$C NMR(100MHz, CDCl$_3$) δ 172.6, 168.1, 147.8, 145.3, 144.5, 144.3, 143.0, 141.3, 140.1, 130.8, 129.3, 129.1, 125.8, 121.2, 120.7, 118.2, 118.1, 114.1, 114.1, 113.4, 109.8, 101.9, 64.6, 61.1, 60.4, 60.0, 59.7, 59.5, 55.2, 54.7, 54.6, 42.2, 41.8, 41.6, 39.6, 28.8, 24.2, 20.5, 15.8, 9.7;

Synthesis of Compound 6-4

To the CH$_2$CN (0.3 ml) and H$_2$O (0.2 ml) mixed solution of the compound 6-3 (2.4 mg, 0.031 mmol, 1.0 equivalent), AgNO$_3$ (10.2 mg, 0.060 mmol) was added and stirred at room temperature for 17 hours. EtOAc was added to the reaction solution, washed by saturated NaHCO$_3$ aqueous solution and the organic layer was dried by Na$_2$SO$_4$. Then concentrated by vacuum, and the compound 6-4 was obtained as a yellow film. Physical properties of the Compound 6-4 are shown in Table 37.

TABLE 37

Compound 6-4

[α]$D^{22}$−58.0° (c=0.15, CH$_2$Cl$_2$); IR(neat film)3347, 2930, 1763, 1741, 1590, 1509, 1458, 1431, 1369, 1237, 1195, 1122, 1109, 1088, 1053, 1029, 1003, 958, 916cm$^{-1}$; $^1$H NMR(400MHz,) δ 6.61(s, 1H), 6.47(s, 1H), 6.45(s, 1H), 6.02(s, 1H), 5.94(s, 1H), 5.69 8br, 1H), 5.39(br, 1H), 5.13(d, J=11.2Hz, 1H), 4.81(s, 1H), 4.48(d, J=3.3Hz, 1H), 4.48(br, 1H), 4.16(d, J=5.1Hz, 1H), 4.05(dd, J=11.2Hz, 1H), 3.79(s, 3H), 3.62(s, 3H), 3.57 8d, J=4.9Hz, 1H), 3.22 (br, 1H), 3.12(ddd, J=10.0, 10.0, 4.0Hz, 1H), 2.82-2.97(m, 2H), 2.81(m, 1H), 2.60(ddd, J=15.9, 10.0, 4.0Hz, 1H), 2.48(ddd, J=15.9, 4.0, 3.4Hz, 1H), 2.37(br, 1H), 2.32(s, 3H), 2.27(s, 3H),

TABLE 37-continued

Compound 6-4

2.20(s, 3H), 2.19(br, 1H), 2.03(s, 3H); $^{13}$C NMR(100MHz, CDCl$_3$) δ 172.6, 168.3, 147.7, 145.1, 144.4, 144.2, 142.9, 141.3, 140.5, 131.5, 129.2, 129.1, 121.8, 120.9, 117.9, 115.9, 114.0, 112.5, 109.8, 101.7, 82.1, 64.7, 61.3, 60.4, 57.8, 57.7, 56.0, 55.1, 54.9, 42.2, 42.1, 41.4, 39.7, 28.9, 24.1, 20.5, 15.8, 9.7;

| Illustration list of abbreviations | |
|---|---|
| MOMO: | methoxymethoxy |
| TFA: | trifluoroacetic acid |
| TF: | trifluoromethansulfonyl |
| Silyl groups | |
| TIPS:. | tri isopropylsilyl group |
| TBS: | t-butyldimethyl silyl group |
| TBDPS: | t-butyl diphenyl silyl group |
| TES: | triethylsilyl group |
| TMS: | trimethylsilyl group |
| Dppf: | diphenyl phosphiferrocene |
| Ts | p-toluenesulfonyl |
| CSA: | camphor sulfonic acid |
| Bn: | benzyl |
| TMG: | N,N,N,N-tetramethylguanidine |
| PMP: | paramethoxyphenyl |
| TABF: | tetrabutylammonium florid |
| DMAP: | dimethylaminopyridine |
| Ms: | methansulfonyl |
| TEM: | triethylamine |
| Boc: | tertiary buthoxycarbonyl |
| Dba: | trans,trans-dibenzylidene acetone |
| Troc: | trichloroethoxycarbonyl |
| G/GHNO$_3$: | guanidineaqueous solution |
| Red-Al: | [(MeOCH$_2$CH$_2$)$_2$AlH$_2$] Na |
| Alloc: | allyloxycarbonyl |
| WSCDD•HCl: | 1-(dimethylaminopropyl)-3-ethylcarbodiimide hydrochloric acid salt |
| DBU: | diazabicyclo[5,4,0]undecene-7-en |

INDUSTRIAL APPLICABILITY

As mentioned above, by utilizing the intermediates and reaction processes of the present invention, various intermediates and analogues of Et743 can be provided, further excellent effect that these compounds can be effectively produced is provided.

The invention claimed is:

1. An intermediate compound for total synthesis of ecteinascidins having a backbone of a five-membered ring structure of ecteinascidins comprising, a compound represented by formula 2 having an OH group at the C4 site,

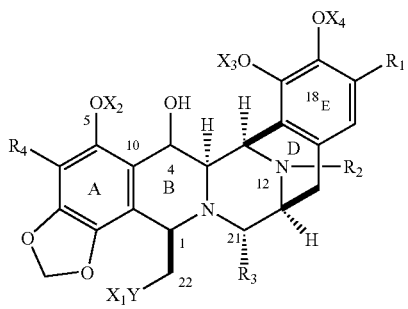

formula 2 wherein, Y is oxygen or NH, X$_1$ is hydrogen or a protecting group of an amino group or Ac, X$_2$, X$_3$ and X$_4$ are independently selected from the group consisting of H or an alkyl group of carbon number 4 or less, alkoxyalkyl group, allyl group, or arylsulfonyl group, R$_1$ and R$_4$ are H or an alkyl group of carbon number 4 or less, R$_2$ is alkoxycarbonyl group which can be substituted by halogen, lower alkyl sulfonyl or aryl sulfonyl group, and R$_3$ is CN or OH.

2. The intermediate compound for total synthesis of ecteinascidins of claim 1, wherein, Y is O, X$_1$ is selected from silyl groups consisting of an acyl group of carbon number 4 or less, t-butyldiphenylsilyl (TBDPS), triisopropylsilyl (TIPS), t-butyldimethylsilyl (TBS), triethylsilyl (TES) and trimethylsilyl (TMS), X$_2$ and X$_3$ are allyl groups, or alkyl groups of carbon number 4 or less or alkoxyalkyl groups, R$_3$ is CN and R$_4$ is an alkyl group of carbon number 4 or less.

3. The intermediate compound of claim 1 as represented by formula 2, produced by the processes displayed by reactions 4-1, 4-2, 4-3, 4-4, 4-5, 4-6, 4-7, 4-8 and 4-9, reaction 4-1

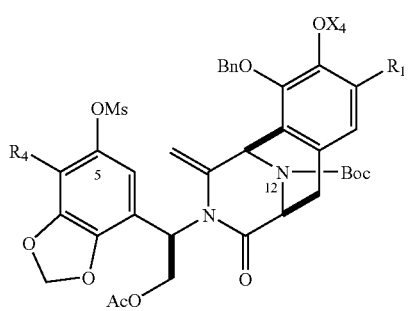

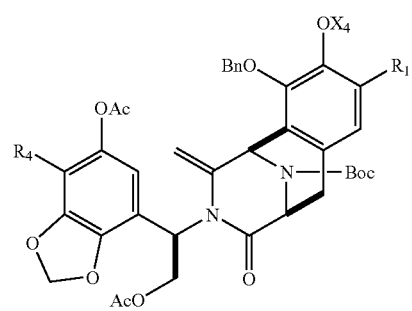

49
-continued
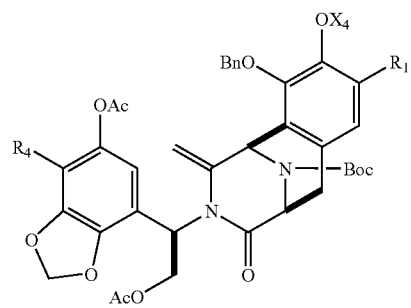
reaction 4-2 TrocCl
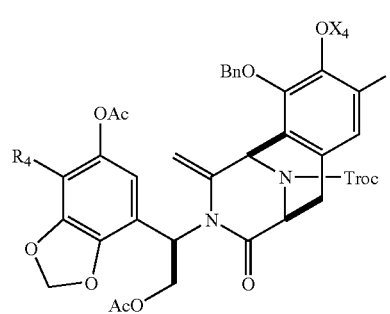
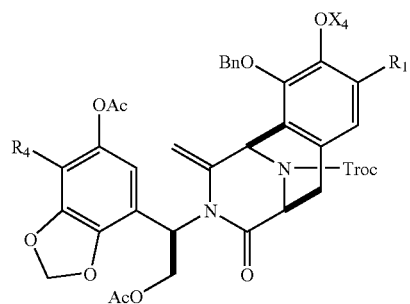
50
-continued
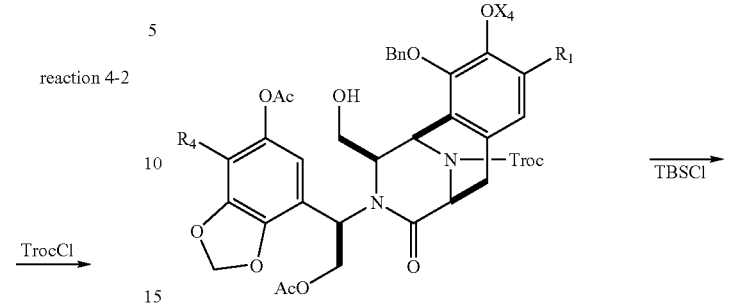
reaction 4-4 TBSCl
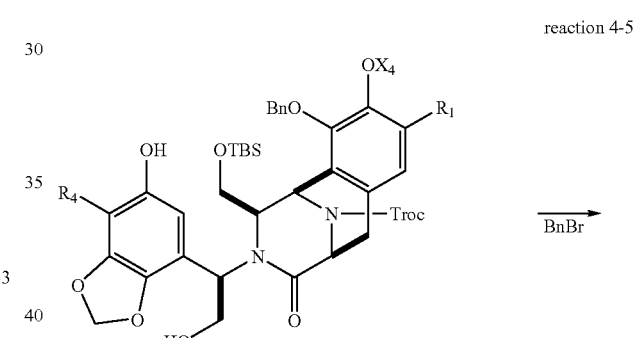
reaction 4-5 BnBr
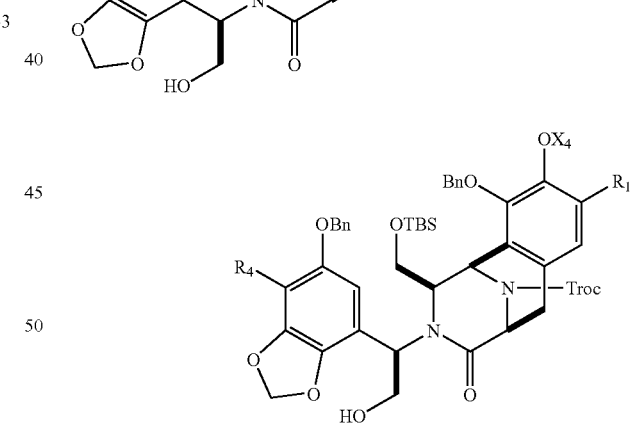
reaction 4-6
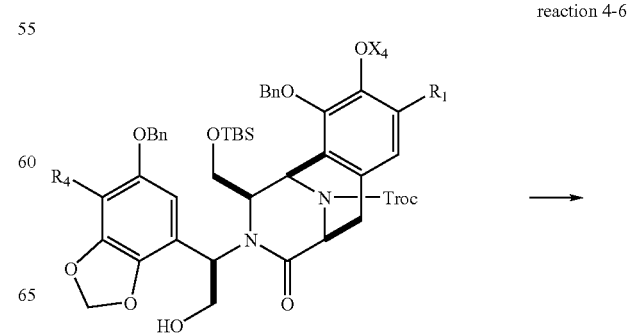

-continued

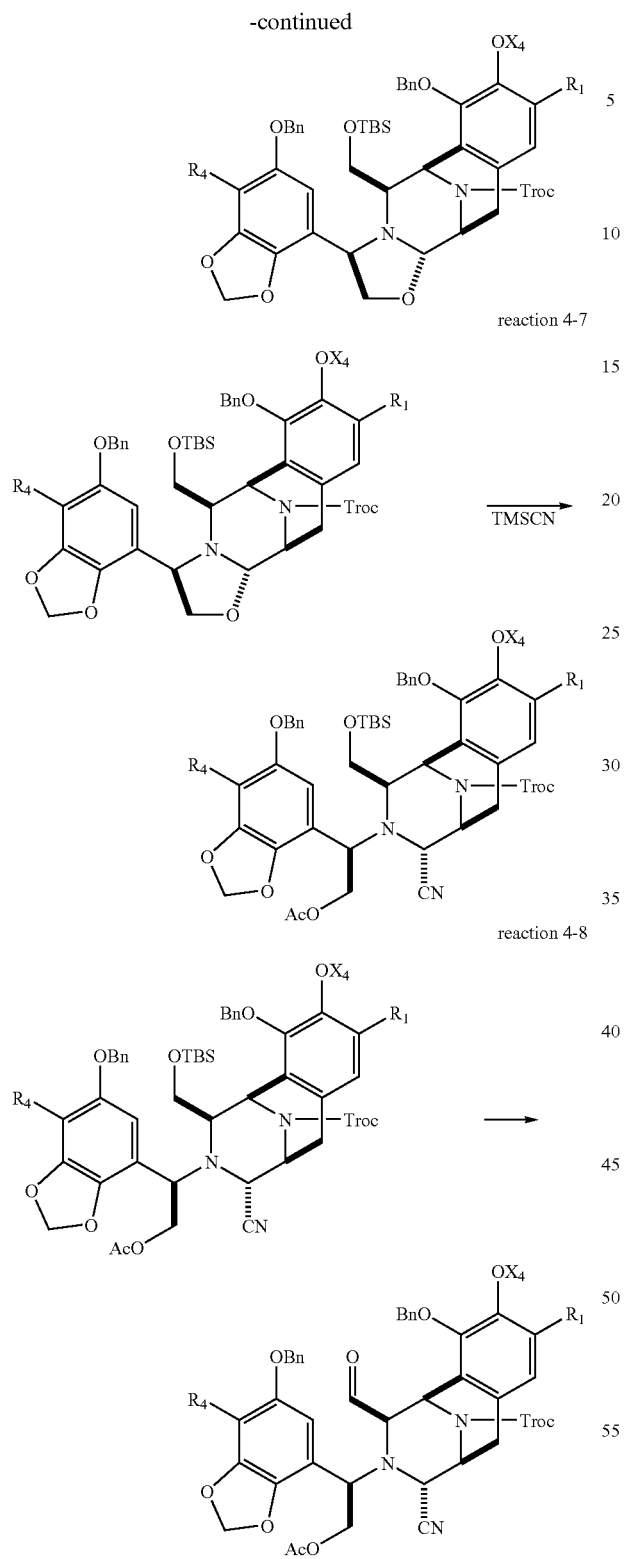

reaction 4-7 reaction 4-8

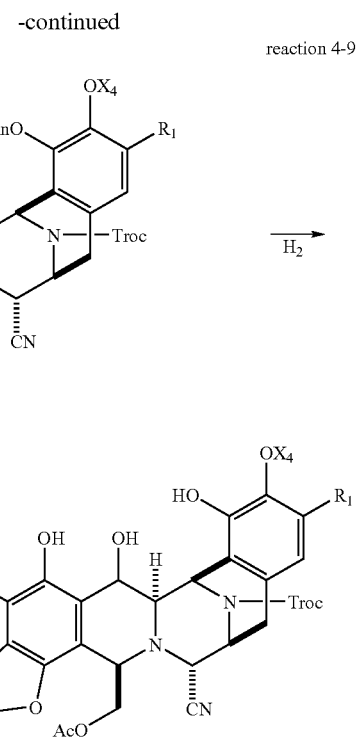

reaction 4-9 wherein the reaction 4-1 is a transforming reaction of $C_5$ mesiloxy group to an acetyl group, the reaction 4-2 is a transforming reaction of $N_{12}$ butoxycarbonyl group to a trichloroethyl group, the reaction 4-3 is a hydration reaction of $C_{3-4}$ double bond, the reaction 4-4 is a transforming reaction of $C_4$ hydroxyl group to a t-butyldimethylsilyl (TBS) group and a transforming reaction of $C_{22}$ and $C_5$ acetyl group to a hydroxyl group, the reaction 4-5 is a transforming reaction of $C_5$ hydroxyl group to a benzyl group, reaction 4-6 is a reducing reaction of $C_{21}$ amide and a ring closing reaction of oxazolidine, the reaction 4-7 is a ring opening reaction of oxazolidine and a transforming reaction of $C_{22}$ hydroxyl group to an acetyl group, the reaction 4-8 is an oxidation reaction of $C_2$ hydroxyl group to an aldehyde and the reaction 4-9 is a transforming reaction of $C_5$, $C_{18}$ benzyloxy groups to a hydroxyl group and a ring forming reaction of B ring, wherein, Y is O, $X_2$ is H, $X_3$ is H, $R_3$ is CN, $X_1$ is Ac, $X_4$, $R_1$ and $R_4$ are the same as formula 2.

4. The intermediate compound for total synthesis of ecteinascidins of claim 1, wherein the substituent $R_2$ of $N_{12}$ site is trichloroethoxycarbonyl (Troc) to which various substituents can be introduced by mild conditions.

* * * * *